(12) United States Patent
Sablotsky et al.

(10) Patent No.: US 11,273,239 B2
(45) Date of Patent: Mar. 15, 2022

(54) BREAST MILK EXPRESSION APPARATUS AND SYSTEM

(71) Applicant: IMALAC, INC., Miami, FL (US)

(72) Inventors: Noreen Gordon Sablotsky, Miami, FL (US); Rachael Sablotsky Kish, Miami, FL (US); Kathryn Garriott Sablotsky, Charleston, SC (US); Scott R. Arp, Miami, FL (US); William Thomas Bales, Miami, FL (US); Paul John Grata, Miami Lakes, FL (US); Damian H. Tomlin, Coral Springs, FL (US); Victor M. Gamez, Fort Lauderdale, FL (US); Lisandro Rivera Alvarez, Miramar, FL (US)

(73) Assignee: IMALAC, INC., Miami, FL (US)

( * ) Notice: Subject to any disclaimer, the term of this patent is extended or adjusted under 35 U.S.C. 154(b) by 16 days.

(21) Appl. No.: 16/485,122

(22) PCT Filed: Feb. 9, 2018

(86) PCT No.: PCT/US2018/017624
§ 371 (c)(1),
(2) Date: Aug. 9, 2019

(87) PCT Pub. No.: WO2018/148546
PCT Pub. Date: Aug. 16, 2018

(65) Prior Publication Data
US 2019/0381225 A1 Dec. 19, 2019

Related U.S. Application Data

(63) Continuation-in-part of application No. 15/431,644, filed on Feb. 13, 2017, now Pat. No. 10,426,877.
(Continued)

(51) Int. Cl.
*A61M 1/06* (2006.01)
*A61H 15/00* (2006.01)

(52) U.S. Cl.
CPC ............... *A61M 1/06* (2013.01); *A61H 15/00* (2013.01); *A61M 2205/50* (2013.01); *A61M 2205/8206* (2013.01)

(58) Field of Classification Search
CPC ........ A61M 1/06; A61M 1/062; A61M 1/064; A61M 1/066; A61M 1/068; A61M 1/007;
(Continued)

(56) References Cited

U.S. PATENT DOCUMENTS 5,235,974 A * 8/1993 Miller ................... A61F 7/007
219/211
5,514,166 A 5/1996 Silver et al.
(Continued)

FOREIGN PATENT DOCUMENTS

WO WO2016/014494 A1 1/2016

OTHER PUBLICATIONS

Supplemental EP Search Report and Opinion dated Nov. 4, 2020 of Application No. EP18751317.
(Continued)

*Primary Examiner* — Kevin C Sirmons
*Assistant Examiner* — Leah J Swanson
(74) *Attorney, Agent, or Firm* — Gordon & Jacobson, P.C.

(57) ABSTRACT

A breast milk expression apparatus includes at least one compression pad disposable about a breast of a user and configured for radial displacement relative to the breast. The apparatus includes a compression unit coupled to the at least one pad, configured to cyclically displace the at least one pad radially inwardly to cause compression of the breast
(Continued)

and, following compression of the breast, permitting the breast to expand and decompress.

28 Claims, 20 Drawing Sheets

Related U.S. Application Data

(60) Provisional application No. 62/594,857, filed on Dec. 5, 2017.

(58) Field of Classification Search
CPC .......... A61M 2210/1007; A61M 1/067; A61M 1/069; A61M 1/0693; A61M 1/06935; A61M 1/0697
See application file for complete search history.

(56) References Cited

U.S. PATENT DOCUMENTS

| | | | | |
|---|---|---|---|---|
| 6,241,715 | B1 * | 6/2001 | Houser | A61F 7/02 450/37 |
| 6,440,100 | B1 | 8/2002 | Prentiss | |
| 6,461,324 | B1 | 10/2002 | Schlensog | |
| 10,279,091 | B1 * | 5/2019 | Jones | A61M 1/064 |
| 2003/0073951 | A1 | 4/2003 | Morton et al. | |
| 2005/0234370 | A1 | 10/2005 | Beal et al. | |
| 2006/0106334 | A1 | 5/2006 | Jordan | |
| 2007/0219486 | A1 * | 9/2007 | Myers | A61M 1/064 604/74 |
| 2014/0249545 | A1 * | 9/2014 | Hyodo | A61B 34/30 606/130 |
| 2014/0378946 | A1 | 12/2014 | Thompson et al. | |
| 2015/0065994 | A1 * | 3/2015 | Fridman | A61M 1/068 604/514 |
| 2017/0112983 | A1 | 4/2017 | Thorne et al. | |

OTHER PUBLICATIONS

Toworld 18 New Electronic Breast Massager Device Augmentation Lift, product description, downloaded Dec. 27, 2016, available at https://www.amazon.com/Toworld18-Electronic-Breast-Massager-Augmentation/dp/B00IZ4W2HM.

Hands-Free Compression for Breast Compression by Lilu., Aug. 22, 2016, as reprinted from Wayback Machine, archived at https://web.archive.org/web/20160822070905/wearlilu.com.

Search Report and Written Opinion dated Apr. 27, 2018 of Application No. PCT/US 18/17624.

CN Office Action and Search Report dated Sep. 3, 2021 of Application No. 201880011637.7.

* cited by examiner

BREAST MILK EXPRESSION APPARATUS AND SYSTEM

CROSS-REFERENCE TO RELATED APPLICATIONS

This application is the national stage of International Patent Application No. PCT/US2018/017624, filed Feb. 9, 2018, which claims priority to U.S. patent application Ser. No. 15/431,644, filed Feb. 13, 2017, and to U.S. Provisional Patent Application No. 62/594,857, filed Dec. 5, 2017, the entire contents of which are incorporated herein by reference.

BACKGROUND

1. Field

This disclosure relates to a breast milk expression apparatus and system.

2. State of the Art

Women's breasts are made of specialized tissues that produce milk. This includes glandular as well as fatty tissues. The milk-producing part of the breast is organized into 15 to 20 sections, called lobes. Within each lobe are smaller structures, called lobules, where milk is produced. The milk travels through a network of tiny tubes called ducts. The ducts connect and come together into larger ducts, which eventually exit the skin in the nipple. There is a considerable body of evidence in the literature on the proven and potential benefits of breast milk expression during lactation. These benefits include, but are not limited to: clearing clogged milk ducts, assisting milk to flow more freely through the ducts resulting in a decrease in time required and increase in quantity of milk expressed during any given single pumping event, creation of subjective physical pleasure and decrease in generalized breast pain, increase in the positive caloric nutritional value of the breast milk resulting from more complete emptying of all lactation tissue. Hand expression is often used as a viable method for milk extraction, and is more commonly recommended by leading lactation experts as a simultaneous adjunct to breast pumping.

SUMMARY

As will be appreciated from the following description, in accordance with at least one aspect, a breast milk expression apparatus and system can replace manual (by hand) milk extraction.

According to one aspect, further details of which are provided below, a breast milk expression apparatus includes an outer shell, and a plurality of circumferentially spaced inner pads coupled to the outer shell. The pads are configured to engage a breast of the user and configured for radial displacement. The breast milk expression apparatus further includes a compression unit coupled to the plurality of pads. The compression unit is configured to cyclically displace the pads radially inwardly against the breast to cause compression of the breast and, following compression of the breast, to permit displacement of the pads radially outwardly from the breast to allow for decompression of the breast.

The outer shell, which may be manufactured in multiple sizes, may have an inner surface that is generally concave. The inner surface may be convex near an axillary part of the breast. The sizes of the outer shell may correspond to bra cup sizes. The inner surface may be configured to engage a maximum possible volume of a user's breast tissue. The outer shell may define a central opening about which the plurality of inner pads are circumferentially spaced. The central opening may be dimensioned to receive a breastshield therethrough for engagement with the user's breast. Milk expressed during use of the breast milk expression apparatus may be directed by the breastshield away from the breast, such as to a collection bottle.

The pads that are coupled to the outer shell may be variously shaped and configured to engage the outer surface of a user's breast for breast manipulation to facilitate milk expression. Also, at least one of the pads may be heated.

The breast milk expression apparatus may include an outer cover that may cover the outer shell. The outer cover may function to protect the outer shell and/or the compression unit and may also provide a desired aesthetic look. The breast milk expression apparatus may also include an inner liner to cover the pads coupled to the outer shell. The inner liner may provide a comfort barrier between the skin of a user's breast and the pads. In one embodiment, the outer cover and the inner liner are coupled together to form an encasement for the breast milk expression apparatus. The outer cover, inner liner, and the encasement may be removable from the breast milk expression apparatus.

In one embodiment of the breast milk expression apparatus, the compression unit includes a cable banded about and through the plurality of pads, and a drive unit coupled to the cable and the outer shell. The drive unit is configured to tighten the cable about the pads to cause the pads to compress the breast and is configured to subsequently loosen the cable about the pads, permitting the breast to expand and decompress.

Each pad may define a circumferential channel through which the cable extends. The circumferential channel may permit relative movement between the cable and the pad. The drive unit may include an electric motor configured to drive a transmission system to alternate tension in the cable. In one embodiment, the drive unit is configured to receive at least one of power and control setting signals from a controller. The drive unit may vary one or more of a pressure applied by the pads to the breast, a duration of compression and decompression, and a heating level of the pads.

At least one of the pads and the outer shell may be made of one or more polymeric materials, such as ABS, nylon, polyurethane, and silicone, and may have a Shore hardness of 10 A to 90 D.

According to another aspect, further details of which are provided below, a breast milk expression system includes at least one breast milk expression apparatus configured to cyclically compress and allow decompression of a breast of a user, at least one strap coupled to the breast milk expression apparatus and configured to position the breast milk expression apparatus on a user's breast, and a controller configured to control the operation of breast milk expression apparatus. The breast milk expression apparatus of the breast milk expression system may be any of the previously described breast milk expression apparatuses. The breast milk expression system may be used for milk expression of one or both breasts of a user, individually or simultaneously.

The controller may be configured to control one or more of breast manipulation pressure, temperature, and manipulation speed. The controller may be wired or wireless. The breast milk expression apparatus of the system may include a power supply to power at least one of the breast milk expression apparatuses and the controller. The controller may include a power supply to power at least one of the controller and one or both of the breast milk expression apparatuses. The controller and/or the breast milk expression apparatus(es) may be operated through a computing device, such as a smart phone, tablet computer, smart watch, or other computing device communicatively coupled to the controller and/or the breast milk expression apparatus(es).

In one embodiment of the system, two breast milk expression apparatuses and a set of straps are arranged so that they may be worn like a bra, such as any type of bra known in the art. The straps may be integrated or otherwise attached to the aforementioned cover and/or liner. The straps are adjustable for personalized fit to the wearer. The straps may permit separation of the two breast milk expression apparatuses from one another so that, for example, the straps can be rearranged to wear one breast milk expression apparatus independently of the other breast milk expression apparatus. The breast milk expression apparatuses may be removable from the straps.

In one embodiment, a breast milk expression system includes a separate bra for supporting breasts of a user and at least one breast milk expression apparatus coupled to the bra and positioned between the bra and the breast of the user. The breast milk expression apparatus may be removably coupled to the bra so that the breast milk expression apparatus can be decoupled from the bra so that that bra can be used without the breast milk expression apparatus. The bra may be any type of bra known in the art. The bra may be integrated with or otherwise attached to the aforementioned cover and/or liner.

According one another aspect, a breast milk expression apparatus includes a compression pad configured to substantially surround a breast of a user, and a string coupled to the compression pad and extending circumferentially around an outer surface of the compression pad. The string is configured to slide relative to the outer compression pad. The apparatus also includes a string tensioning unit coupled to at least one end of the string, the string tensioning unit configured to apply tension to the string to cyclically displace the compression pad radially inwardly against the breast to cause compression of the breast and, following compression of the breast, permitting the breast to expand and decompress. According to one embodiment, the breast milk expression apparatus may also include a plurality of beads fixed to the compression pad and through which the string extends. The beads are circumferentially spaced from one another around the outer surface of the compression pad, and the string is configured to slide through the beads.

According to one embodiment, the string tensioning unit includes a motor and a transmission element driven by the motor, the transmission element coupled to the string. The transmission element may include a rack and pinion gear.

According to one embodiment, the breast milk expression apparatus includes a string routing unit for routing at least one end of the strings from the compression pad to the string tensioning unit.

According to one embodiment, the compression pad is configured to connect to a bra that is configured to support the compression pad in engagement with the breast of the user. Also, in one embodiment, the string is configured to automatically radially expand in response to the expansion of the breast following compression of the breast.

According to one embodiment, the compression pad has a tapered outer surface and extends longitudinally from a larger diameter first end to a smaller diameter second end, and the breast milk expression apparatus may include a plurality of strings including a first string located at a first longitudinal position and a second string located at a second longitudinal position that is longitudinally spaced from the first longitudinal position and closer to the second end. If desired, three, four, or even more strings may be utilized. Each of the strings is coupled to the compression pad and extends circumferentially around an outer surface of the compression pad, and each string is configured to slide relative to the outer compression pad. The string tensioning unit may include a motor and a transmission element driven by the motor, the transmission element coupled to the plurality of strings and configured to sequentially tension the strings. Alternatively, in one embodiment, the transmission element is configured to apply tension to all of the strings simultaneously. In one embodiment, the transmission element includes a rack connected to the first string and a pinion gear engaged with the rack and driven by the motor. In one embodiment, the second string is connected to a pull member and the rack includes an engagement member configured to engage the pull member after a predetermined amount of relative translation between the rack and the pull member. In one embodiment, the transmission element is configured to translate the strings linearly relative to one another. In one embodiment, the transmission element is configured to apply tension to the first string for a longer duration than the second string.

According to another aspect, a breast milk expression system includes at least one breast milk expression apparatus configured to cyclically compress a breast of a user and, following compression, permit expansion and decompression of the breast, and at least one bra coupled to the breast milk expression apparatus and configured to position the breast milk expression apparatus on a user's breast.

In one embodiment, the bra has an inner layer and an outer layer and at least a portion of the breast milk expression apparatus is configured to be connected to the bra between the inner and outer layer. In another embodiment, at least a portion of the breast milk expression apparatus is configured to be connected to the bra under the inner layer. In one embodiment, the breast milk expression apparatus includes a compression pad configured to substantially surround a breast of a user, and the compression pad is connected to the inner layer of the bra. Also, the breast milk expression apparatus includes a string coupled to the compression pad and extends circumferentially around an outer surface of the compression pad, and the string is configured to slide relative to the outer compression pad. Further, the breast milk expression apparatus includes a string tensioning unit coupled to at least one end of the string. The string tensioning unit is configured to apply tension to the string to cyclically displace the compression pad radially inwardly against the breast to cause compression of the breast and, following compression of the breast, permitting the breast to expand and decompress.

In one embodiment, the compression pad includes a removable connector configured to removably connect to a connector secured to an inner layer of the bra located about a base of a cup of the bra. In one embodiment, the connector of the compression pad and the connector of the inner layer of the bra slide together. In one embodiment, the connector of the compression pad and the connector of the inner layer of the bra are portions of a zipper closure. In one embodiment, the connector of the inner layer of the bra extends about at least portion of a lower half of the base of the cup.

BRIEF DESCRIPTION OF THE DRAWINGS

FIG. 11b shows an assembly view of a breast milk expression apparatus of the system shown in FIG. 11a.

FIG. 12a show a front view of the bra shown in FIG. 11a.

FIG. 16b is a front view of the breast milk expression apparatus shown in FIG. 16a.

DETAILED DESCRIPTION OF THE PREFERRED EMBODIMENTS

Figure 1A:
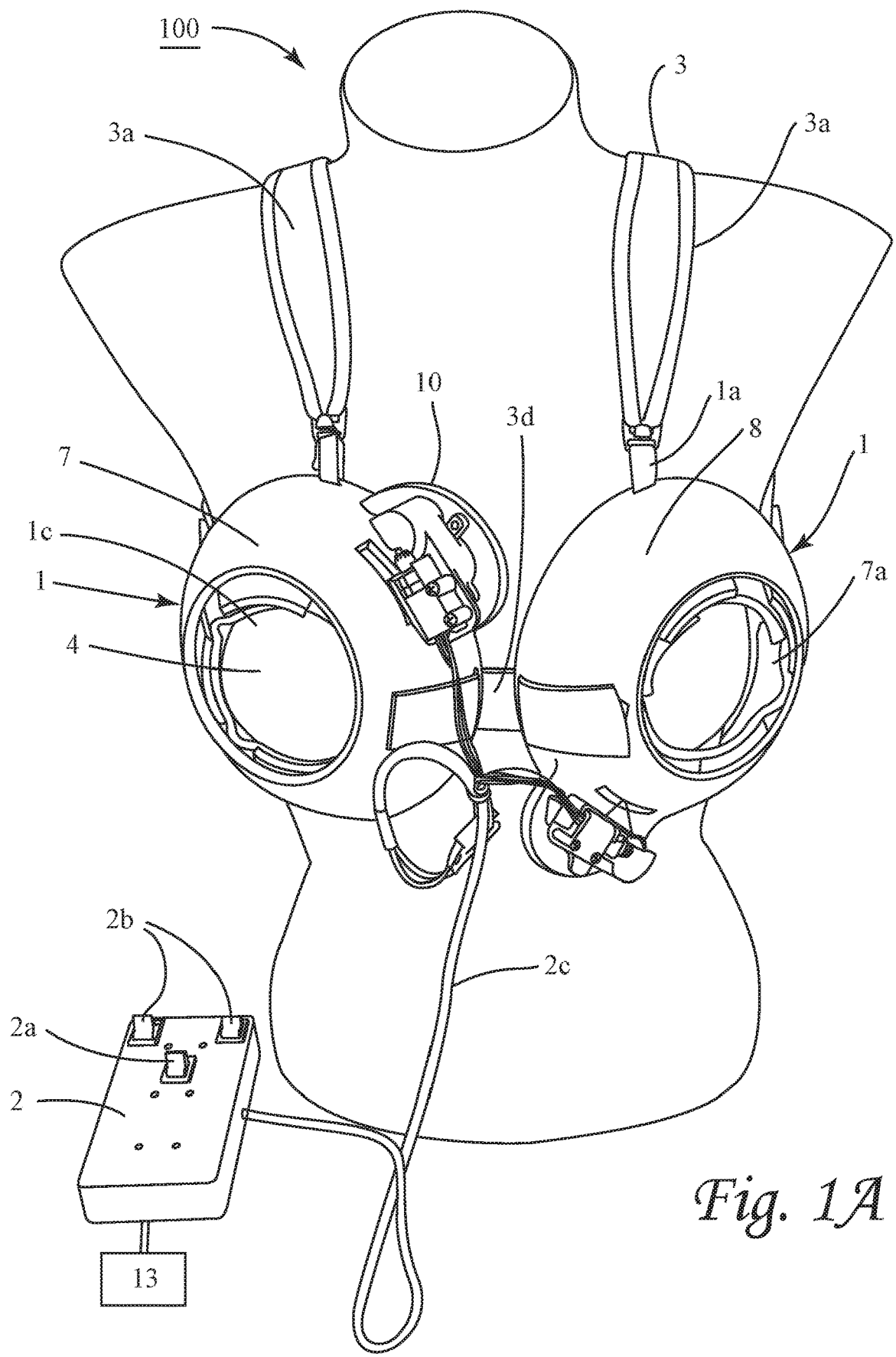
FIGS. 1A and 1B show an embodiment of a breast milk expression system arranged on a torso.

FIG. 1A shows one embodiment of a breast milk expression system 100 that includes two breast milk expression apparatuses 1 (hereinafter referred to as "expression apparatuses"), a controller 2 coupled to the expression apparatuses 1 via a power and control cords 2c, and a plurality of straps 3 for arranging the expression apparatuses 1 on the breasts 4 of a user and for connecting the expression apparatuses 1 together. Preferably, the straps 3 and expression apparatuses 1 are arranged and used like a bra to facilitate hands-free operation of one or both of the expression apparatuses 1. For example, the straps 3 may support the expression apparatuses 1 over the breasts 4 without a user holding the expression apparatuses 1 in place, either when the expression apparatuses are on or off. Two expression apparatuses 1 are shown included with the system 100 in FIG. 1A, where one expression apparatus 1 corresponds to each breast. While two expression apparatuses 1 are shown, they may operate independently or together (e.g., simultaneously). Also, in other embodiments of the system, only one expression apparatus 1 may be included and a user may alternate its use from one breast to another as desired. Each expression apparatus 1 is configured to manipulate the tissue of the corresponding breast 4 based on a control input from the controller 2, as described in greater detail below. The milk expression system 100 can be used before, during, and/or after breast pumping or nursing to facilitate lactation and improve milk production and flow.

Figure 1B:
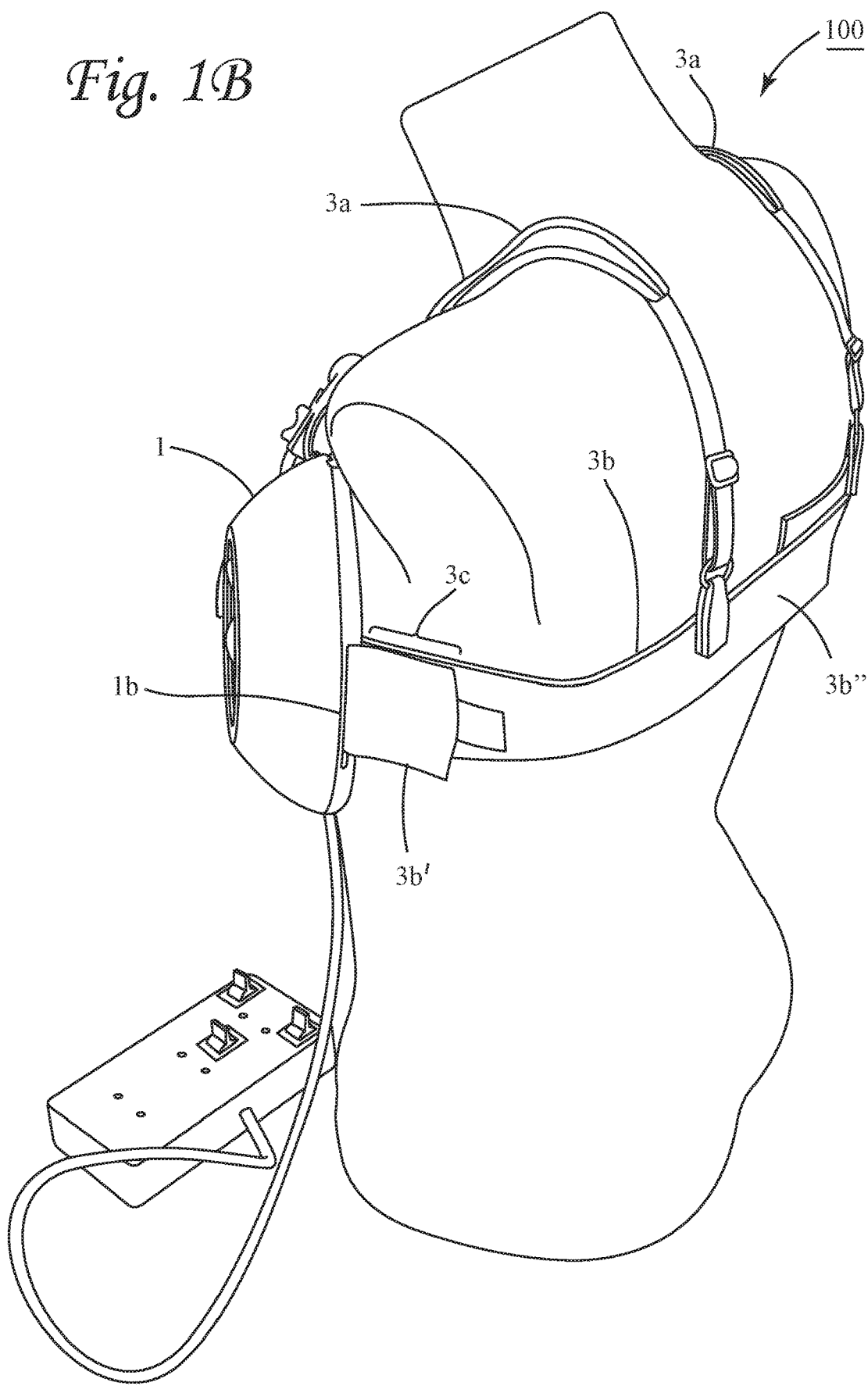

The plurality of straps 3 includes adjustable top straps 3a, each of which is attached at a top location 1a of the expression apparatuses 1. Each top strap 3a is configured to extend upward from a corresponding expression apparatus 1 and go over the shoulders and down the back of the user to connect to a corresponding adjustable side or back strap 3b (hereinafter referred to as a "side strap"), as shown in further detail in FIG. 1B. The top straps 3a may be padded for user comfort. Each side strap 3b has a first end 3b' coupled to an outer, side location 1b (FIG. 1B) of a corresponding expression apparatus 1, and has a second end 3b" opposite the first end 3b'. The side strap 3b extends from the expression apparatus 1 around the side of the user's torso towards the center of the user's back, where the second ends 3b" of each side strap 3b may be fastened together. The second ends 3b" of the side straps 3b may include hooks and loops (not shown) for fastening the second ends 3b" together. Also, the length of the side straps 3b may be adjustable at either end 3b', 3b" thereof. For example, in the embodiment shown in FIG. 1B, each expression apparatus 1 may have a loop or slot on its side 1b through which a first end 3b' of the side strap 3b can be wrapped. The first end 3b' may have hooks or loops and an overlapping portion 3c of the strap 3b may have mating hooks or loops to adjust the length of the side strap 3b.

In the shown embodiment, a center strap 3d (FIG. 1A) between the user's breasts 4, couples the expression apparatuses 1 together. The expression apparatuses 1 may have loops or slots on inner side locations 1d of the expression apparatuses 1 for coupling ends of the center strap 3d thereto, similar to the loops or slots on the outer side locations 1b of the expression apparatuses 1 for coupling side straps 3b. The length of the center strap 3d may also be adjustable to adjust the spacing between the expression apparatuses 1. The center strap 3*d* may permit decoupling or separation of the two expression apparatuses 1 from one another and from the center strap 3*d*. For example, the ends of the strap 3*d* may be detachably connected to the side locations 1*d* of respective expression apparatuses 1. Also, the center strap 3*d* may be formed as two parts that are connectable at respective ends between the side locations 1*d*, in the same manner that side straps 3*b* connect at ends 3*b*" between side locations 1*b* of expression apparatuses 1.

Figure 1C:
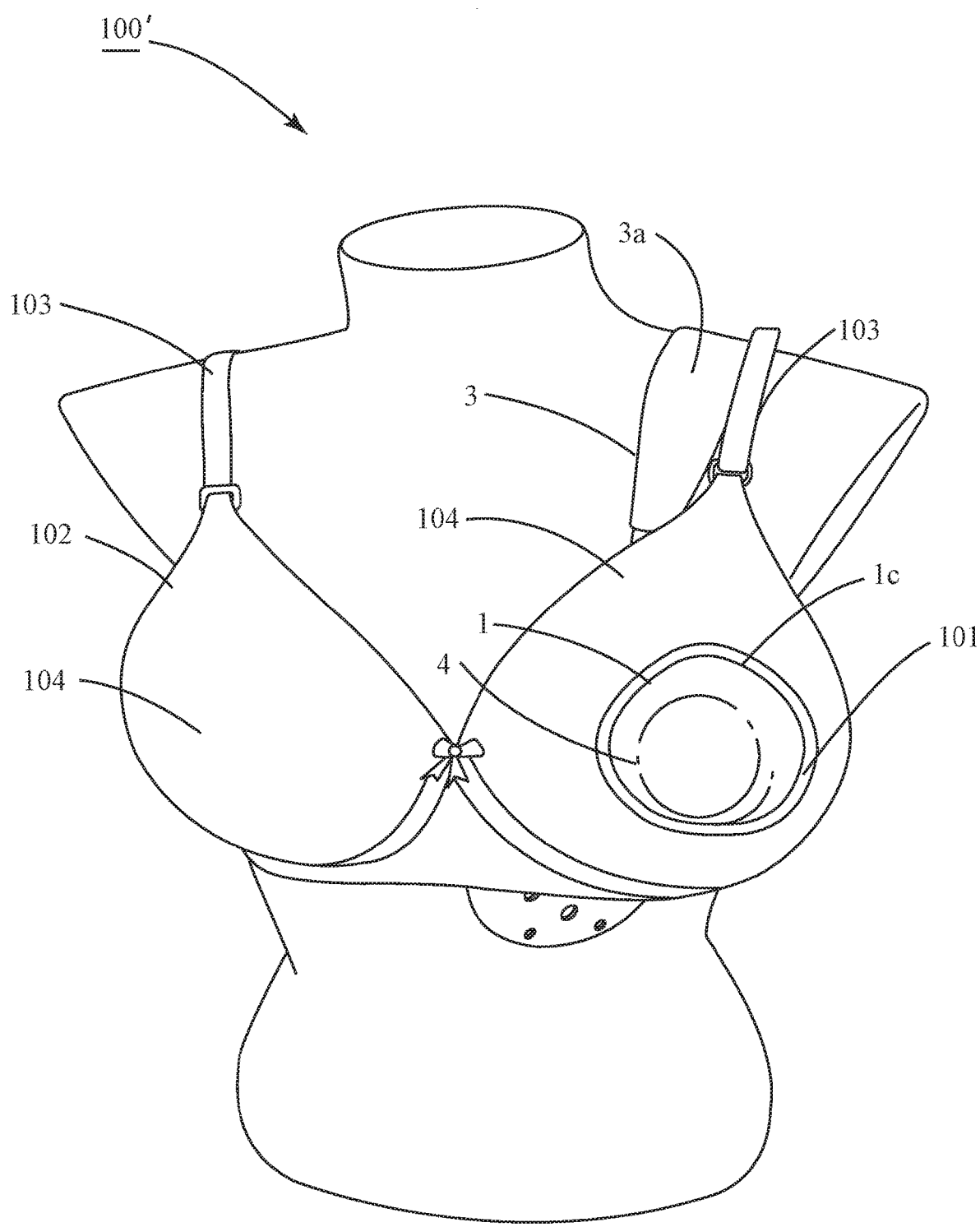
FIG. 1C shows an embodiment of a breast milk expression system that includes a bra and a breast milk expression apparatus of the system of FIGS. 1A and 1B.
Figure 2:
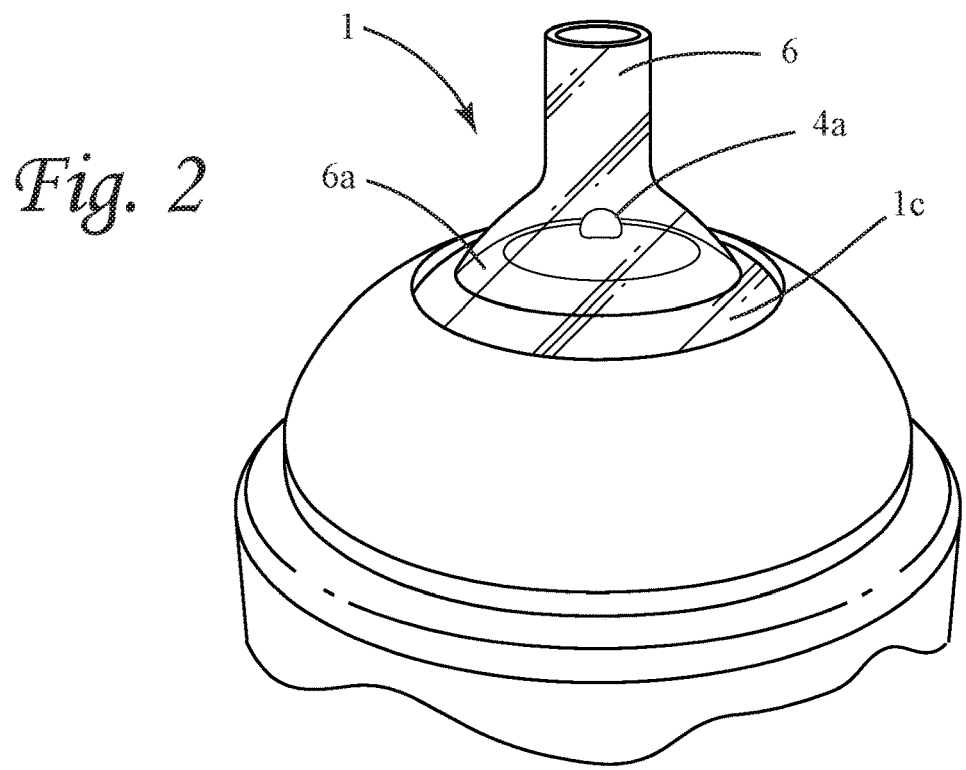
FIG. 2 shows a top perspective view of a breast milk expression apparatus of the system of FIGS. 1A and 1B along with a breastshield.

While the system 100 shows straps 3 and expression apparatuses 1 worn like a bra, in one embodiment shown in FIG. 1C, a system 100' includes a separate bra 102 and at least one breast expression apparatus 1 (partially covered by the bra 102 in FIG. 1C) coupled to the bra 102 and positioned between the bra 102 and the breast 4. The bra 102 may have breast cups 104 attached to one or more straps 103, and one breast expression apparatus 1 may be removably coupled to an inside of a corresponding breast cup 104 so that the expression apparatus 1 can be positioned between the user's breast 4 and the cup 104 of the bra 102. The expression apparatus 1 may be coupled to the breast cup 104 using one or more fasteners or simply held in position by a friction or interference fit between the breast cup 104 and the expression apparatus 1. In such an embodiment, the expression apparatus 1 can be decoupled from the 102 bra (e.g., the cup 104 of the bra 102) so that that bra 102 can be used without the expression apparatus 1.

One or both of the cups 104 of the bra 102 may be solid (e.g., left cup in FIG. 1C) or may have at least one opening 101 (e.g. right cup in FIG. 1C). In the example shown in FIG. 1C, the opening 101 is aligned with opening 1*c* of the expression apparatus 1. The opening 101 may be sized to be at least as large as the opening 1*c*.

Although FIG. 1C shows one example bra, the aforementioned bras may be any type of bra known in the art, including, without limitation, a halter bra, a bandeau bra, a balconette bra, a contour or molded cup bra, a convertible bra, a demi cup bra, a full cup bra, a mastectomy bra, a maternity and nursing bra, a minimizer bra, a padded bra, a plunge bra, a push-up bra, a racerback bra, a shelf bra, a sports bra, a strapless bra, a T-shirt bra, and a U-plunge bra.

In use, the expression apparatuses 1 of the breast milk expression system 100 are positioned over and about the breasts 4. As shown in FIGS. 1A to 3, the expression apparatuses 1 define a central opening 1*c* in which a nipple 4*a* of the breast 4 can be positioned. The central opening 1*c* provides access for a user to position a breastshield 6 (FIG. 2) within the opening 1*c* over the nipple 4*a* to facilitate milk collection (e.g., into a bottle or by breast pumping) while using the system 100. Preferably, the diameter of the central opening 1*c* is large enough to accommodate a range of sizes of breastshields 6 being marketed. For example, the diameter of the central opening 1*c* may be large enough to accommodate a breastshield having a diameter of 36 mm.

Figure 3:
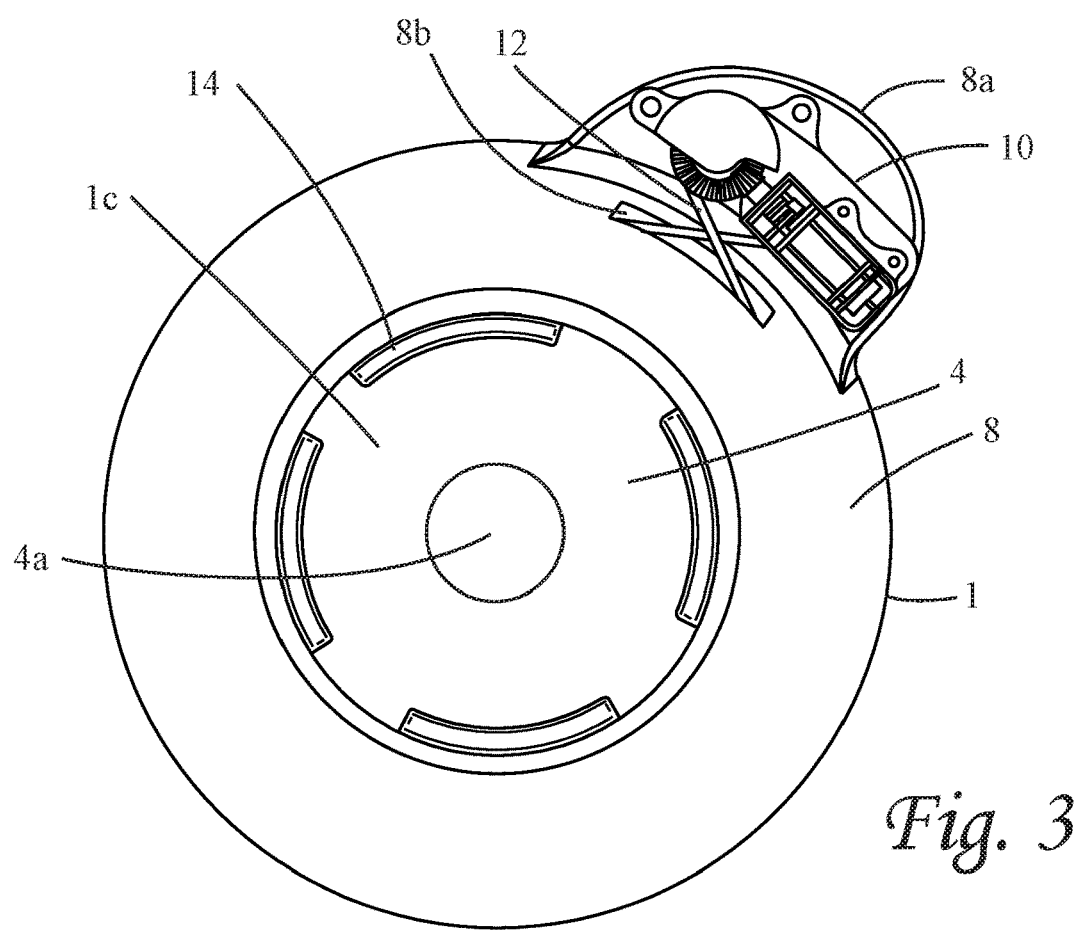
FIG. 3 illustrates a top view of one of the breast milk expression apparatuses shown in FIG. 1A.

In the breast milk expression system 100, each expression apparatus 1 is functionally identical. FIG. 3 shows a view of one of the expression apparatuses 1 shown in FIG. 1A. The expression apparatus 1 has an outer shell 8, which may be made of ABS, nylon, polyurethane, or silicone having a Shore hardness of about 10 A to 90 D. The outer shell 8 has an inner form that is generally concave to conform to the contour of a plurality of pads 14, further details of which are provided below. Also, in one embodiment of an expression apparatus 201 (FIG. 7), an outer shell 208 has a portion 208*c* (FIGS. 9, 10) that is configured to extend over or near an axillary part 4*b* (FIG. 10) of the breast 4, as shown in FIG. 10. An inner surface 208*d* (FIG. 9) of the outer shell 208 is generally concave, and may be convex on portion 208*c* to conform to the contour of the axillary part 4*b* (FIG. 10) of the breast 4.

The expression apparatus 1 may include an outer cover 7 that may cover the outer shell 8 and/or the compression unit. The outer cover 7 may function to protect the outer shell and/or the compression unit and may also provide a desired visual appearance. The expression apparatus 1 may also include an inner liner 7*a* to cover the pads 14 coupled to the outer shell 8. The inner liner 7*a* may provide a comfort barrier between the breast 4 and the pads 14. The outer cover 7 and/or inner liner 7*a* may be removable from the expression apparatus 1. The outer cover 7 and/or the inner liner 7*a* may be made from one or more of polyester, cotton, spandex, silk, or other preferably comfortable-to-the-touch material. In one embodiment, the outer cover 7 and the inner liner 7*a* are coupled together to form an encasement for the expression apparatus 1. While the outer shell 8 is shown as being a generally solid structure, in at least one embodiment, the outer shell 8 may be have openings and may take the form of a frame or cage-like structure, which may make the shell 8 lighter and more comfortable for the user to wear.

In at least one embodiment, the breastshield 6 may be incorporated into the expression apparatus 1. For example, a flange 6*a* (FIG. 2) of the breastshield 6 may be removably attachable to and detachable from the outer shell 8, outer cover 7, or inner liner 7*a*. For example, the flange 6*a* of the breastshield 6 may removably engage (e.g., adhesively, friction fit, interference fit, etc.) the outer shell 8, outer cover 7, or inner liner 7*a* to retain the breastshield 6 connected thereto when in use and permits the breastshield 6 to be detached from the outer shell 8, outer cover 7, or inner liner 7*a*, without damage to any of the breastshield 6, the outer shell 8, outer cover 7, and inner liner 7*a*.

The outer shell 8 and pads 14 may be made from one or more fabric materials. The fabric used for the outer shell 8 may be stiffer than the fabric used for the pads 14. Portions of the fabric(s) used may be reinforced or stiffened, such as with a wire, similar to an underwire of a bra. Such a reinforcement or stiffener may be made of at least one of metal, plastic, or resin, for example. Further, the outer shell 8 may be formed as a fabric covered cage or mesh, which may improve comfort for the user, as mentioned above.

The outer shell 8 has a deck 8*a* extending generally horizontally from a side of the outer shell 8. In a case where the outer shell 8 is made of fabric, as discussed above, the deck 8*a* may be formed from stiff fabric and may be reinforced with a reinforcement member or stiffener (e.g., wire), as noted above. The deck 8*a* is configured for mounting and supporting a drive unit 10, further details of which are provided below. For example, the drive unit 10 may be adhesively or mechanically attached to the deck 8*a*. The outer shell 8 also defines a circumferential through-slot 8*b* proximate the deck 8*a* which is configured to route a cable 12, which is driven by the drive unit 10. As will be described in greater detail hereinafter, the drive unit 10 and the cable 12 operate to cyclically compress and allow decompression of the pads 14 against the breast 4 to manipulate the tissue of the breast 4. The drive unit 10 and the cable 12 may thus be considered an embodiment of what is hereinafter termed a "compression unit." Other embodiments of a compression unit are possible. For example, in one embodiment a geared belt or notched strap may be used in place of the cable 12 and such a geared belt or notched strap may be moved by a releasable ratcheting arrangement to tighten the belt or strap and allow the belt or strap to be loosened.

Figure 4:
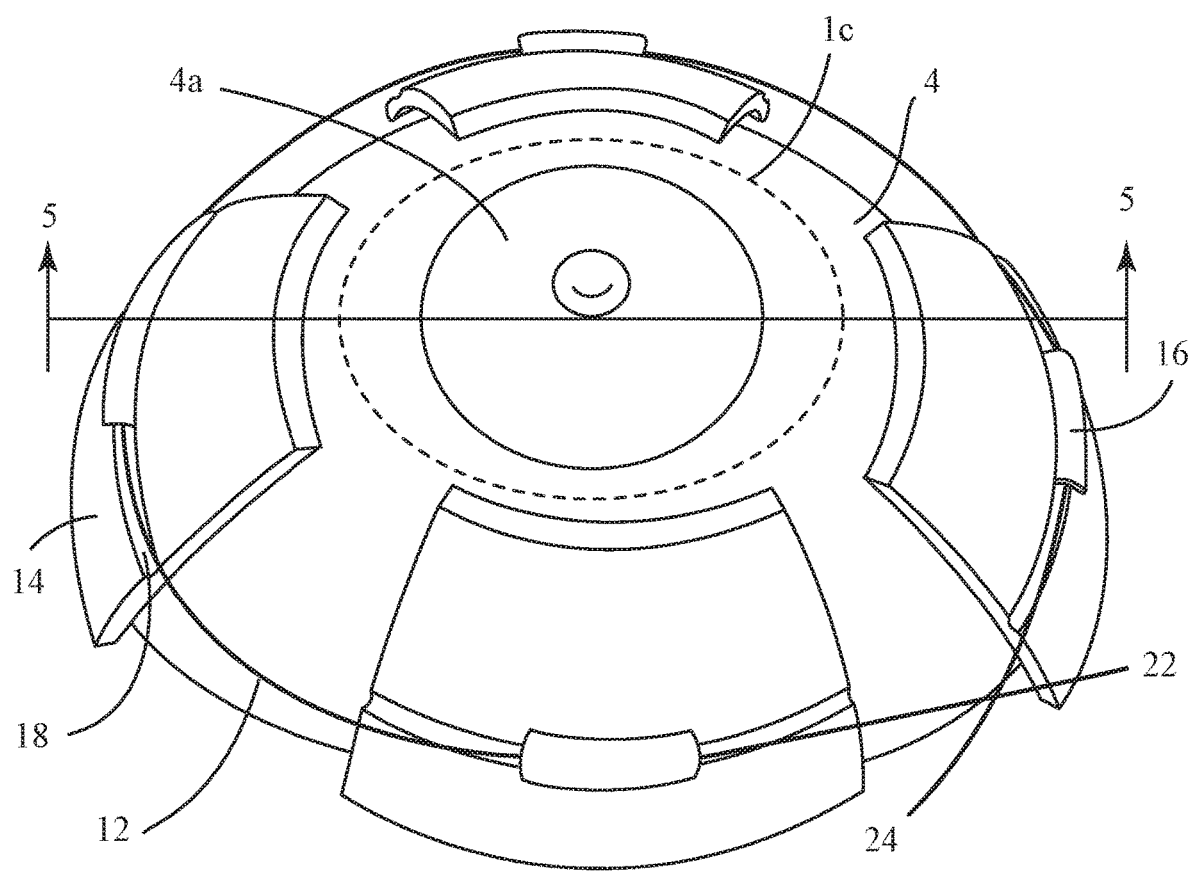
FIG. 4 illustrates the breast milk expression apparatus shown in FIG. 3 with an outer shell omitted to show an arrangement of pads of the breast milk expression apparatus located relative to a breast of the user.

As shown in FIG. 3, the outer shell 8 partially covers a plurality of the pads 14. FIG. 4 shows the pads 14 with the outer shell 8 omitted for clarity. The pads 14 are spaced circumferentially from one another around the central opening 1c. The pads 14 may be made of flexible material, such as polyurethane or silicone. The pads 14 may have a Shore hardness of 10 A to 90 D. The pads 14 are configured to be radially displaced inwardly for a certain period of time by action of the drive unit 10, which moves the pads 14 toward and against the breast 4, compressing the tissue of the breast 4. When the action of the drive unit 10 reverses, the compression ends and the pads 14 can radially expand due to radially outward pressure on the pads 14 applied by the breast 4. This compression/decompression cycle can repeat by operation of the drive unit 10. The parameters of that cycle may be adjusted, start, or stopped by the controller 2, which is communicatively coupled to the drive unit 10, either via a wired connection 2c or a wireless connection (e.g. infra-red, Wi-Fi, Bluetooth, etc.).

In one embodiment at least one or more of the pads 14 may have a heating element (not shown) to warm the breast 4 during operation of the expression apparatus 1. Also, optionally, on an inner side of the pads 14 (e.g., side facing the breast 4), the pads 14 may have one or more padding layers (not shown), such as to improve user comfort and fit. In one embodiment, the pads 14 may contain a gel-like material to facilitate heat dispersion. The gel-like material may include silicone.

Figure 5:
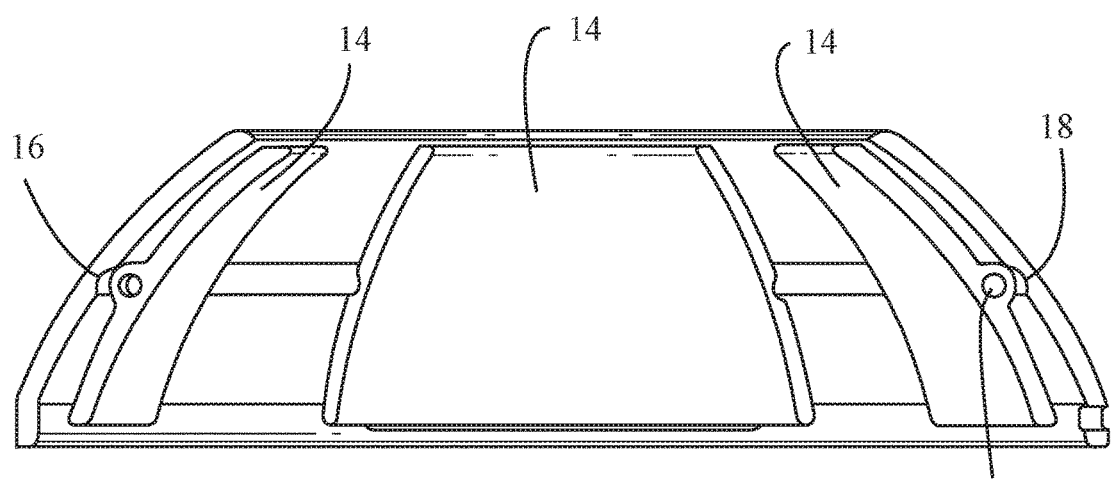
FIG. 5 is a view of the pads of FIG. 4 along section 5-5 shown in FIG. 4, and with the breast omitted.

As shown in FIGS. 4 and 5, each pad 14 defines an enclosed cable channel 16 and a groove 18 that extend circumferentially on an outer side of the pad 14. The cable channels 16 and grooves 18 are configured to route the cable 12 around the plurality of pads 14, thereby coupling the pads 14 together. The cable 12 crosses over itself (preferably without touching) between two of the pads 14, as shown in FIGS. 3 and 4. While only one cable channel and groove are shown for each pad 14, each pad 14 may have more than one cable channel and groove to accommodate more than one cable, as will be described in greater detail below.

Figure 6:
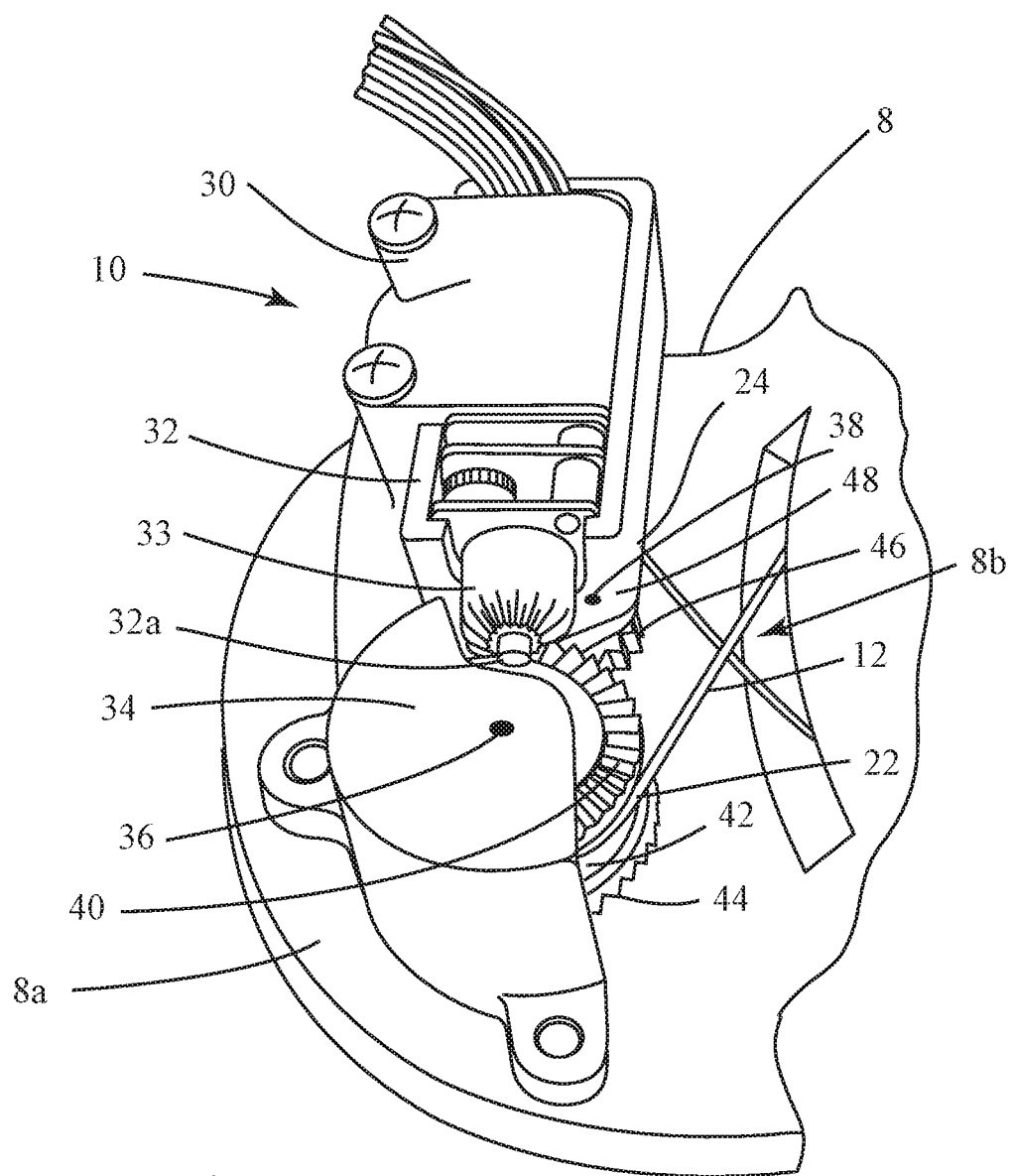
FIG. 6 is an enlarged view of a drive unit of one of the breast milk expression apparatuses shown in FIG. 1A.

As shown in FIG. 6, the cable 12 extends through the circumferential slot 8b in the outer shell 8 and crosses over itself with a first end 22 and a second end 24 extending to the drive unit 10. In the embodiment of the drive unit 10 shown in FIG. 6, the drive unit 10 includes an electric motor 30, a gearbox 32 driven by the motor 30, and a transmission system 34 driven by the motor 30 and connected to the first and second ends 22 and 24 of the cable 12. The motor 30 may be an AC or DC electric motor powered by a power supply included with the expression apparatus 1, such as a battery, or by an external power supply, such as a power supply (e.g., battery) located in the controller 2 and supplied via cord 2c (FIG. 1A). Also, the expression apparatus 1 or the controller 2 may have a power connector for receiving power from an electrical outlet, such as an AC outlet.

The motor 30 may be coupled to the gearbox 32 by one or more gears as is known in the art to drive a driving bevel gear 33 on an output shaft 32a of the gearbox 32. The transmission system 34 includes a first vertical shaft 36 and a second vertical shaft 38 that are driven by the driving bevel gear 33. The first shaft 36 rotates about a first vertical axis along a longitudinal length of the first shaft 36. A driven bevel gear 40 is secured to an upper end of the first shaft 36. The driven bevel gear 40 meshes with and is configured to be driven by the driving bevel gear 33 to rotate the first shaft 36 about the first axis. The first shaft 36 passes through a center of a first pulley 42, which is secured to the first shaft 36 to rotate with the first shaft 36 about the first axis. The first pulley 42 is secured to the first end 22 of the cable 12. A driving gear 44 is secured to a lower end of the first shaft 36 for rotation therewith.

The second shaft 38 extends parallel to the first shaft 36 and the second shaft 38 is configured to rotate about a second vertical axis along a longitudinal length of the second shaft 38. A driven gear 46 is secured to a lower end of the second shaft 38 and is configured to rotate about the second axis with the second shaft 38. The driven gear 46 is enmeshed with the driving gear 44, which drives the driven gear 46 and rotates the second shaft 38 when the first shaft 36 rotates. However, the direction of rotation of the first and second shafts 36 and 38 is opposite (i.e., clockwise and counterclockwise or vice versa depending on the direction of movement of the motor). The second shaft 38 extends through a center of a second pulley 48, which is secured to the second shaft 38 for rotation with the second shaft 38 about the second axis. The second end 24 of the cable 12 is secured to the second pulley 48. An upper end of the second shaft 38 is preferably supported by a housing of the motor 30. As a result of the gearing of the transmission system 34, when the motor 30 operates so as to rotate the driving bevel gear 33 in a clockwise direction, the first shaft 36 and first pulley 42 are rotated clockwise, and the second shaft 38 and the second pulley 48 are rotated counter-clockwise so that a certain length of the cable 12 from its respective ends 22 and 24 will be taken up by the respective pulleys, which will draw the pads 14 radially inward relative to opening 1c to cause compression of the breast 4. When the motor 30 reverses direction, the cable 12 slackens (relaxes) allowing the compressed breast 4 to relax and decompress. As the breast 4 decompresses, the tissue of the breast 4 pushes the pads 14 radially outwardly, while at least some of the length of the cable 12 taken up during compression is withdrawn from the pulleys 42 and 48.

Each tensioning and relaxation of the cable 12 which results in compression and permits decompression of the breast may be considered a cycle, which is preferably repeated to effect a breast tissue manipulation, which may cause breast milk expression. Parameters of the cycle(s) can be controlled by the controller 2. For example, the controller 2 may be configured to control the duration of compression and the duration of decompression, which may be the same or different. Also, the controller 2 may be configured to control the tension of the cable 12 during compression (which can control the pressure applied to the breast). The controller 2 has switches and buttons 2a and 2b, which may control the operating parameters as well as to turn the expression apparatuses on and off.

The controller 2 may be configured to operate based on set operating parameters or a real-time operating state of a breast pump apparatus that may be used simultaneously with the system 100 by the user, as discussed above. For example, the user of the system 100 may use the controller 2 to a select a manipulation speed or pressure, such as with the buttons 2a, 2b, based on the operating state of the breast pump to achieve a desired breast pumping result. Specifically, the user may select a certain compression and decompression duration and/or compression pressure based on a breast pumping speed and/or breast pumping pressure setting of the breast pump apparatus to achieve, for example, optimal milk flow rate or a desired level of comfort.

Alternatively or additionally, the controller 2 may be communicatively coupled (via wired or wireless connection) to a computing device 13 (FIG. 1A), such as personal computer, smart phone, smart watch, or tablet computer, which can set and control the operation of the expression apparatus(s) 1. The computing device 13 may be coupled to a graphical display device (e.g., a screen). The computing device 13 may execute software (e.g. an application, a.k.a., an "app") that causes the display device to graphically display an operational interface to a user. The operational interface may be used to configure and/or control the expression apparatuses 1. For example, the operational interface may include virtual controls (e.g., on-screen buttons) that may replicate the physical buttons 2a, 2b of controller 2, and may provide information to the user about an operating status of the system 100. By way of example, and not limitation, such information may include current operating setting(s), elapsed time of use, heater temperature level, and breast skin temperature. The provided information may be saved locally or remotely for retrieval and/or analysis.

In one embodiment, the controller 2 may be communicatively coupled (via a wired or wireless connection interface) to a breast pump apparatus to automatically control the operation of the system 100 based upon the operation of the breast pump apparatus. For example, the controller 2 may automatically synchronize the operation of one or both expression apparatuses 1 of the system 100 with the breast pump apparatus based on feedback received directly from the breast pump apparatus or from a user of the breast pump apparatus. In one embodiment, a closed-loop feedback system may include a sensor that monitors a rate of milk production of the breastfeeding apparatus. The rate of milk production can be used as an input to the controller 2 as a basis to adjust operating parameters and settings of the system 100 so as to regulate the rate of milk production.

Figure 7:
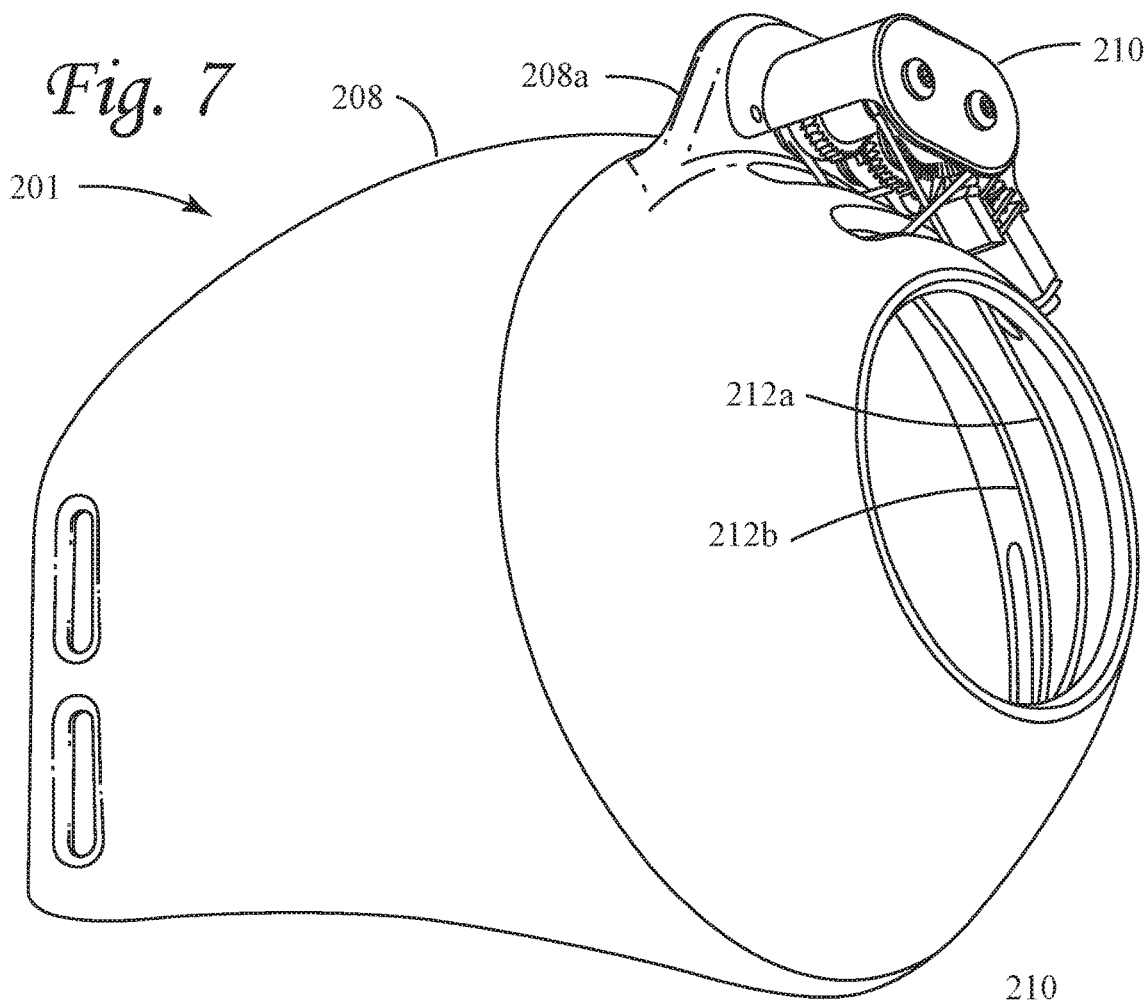
FIG. 7 shows a perspective view of another embodiment of a breast milk expression apparatus.
Figure 8:
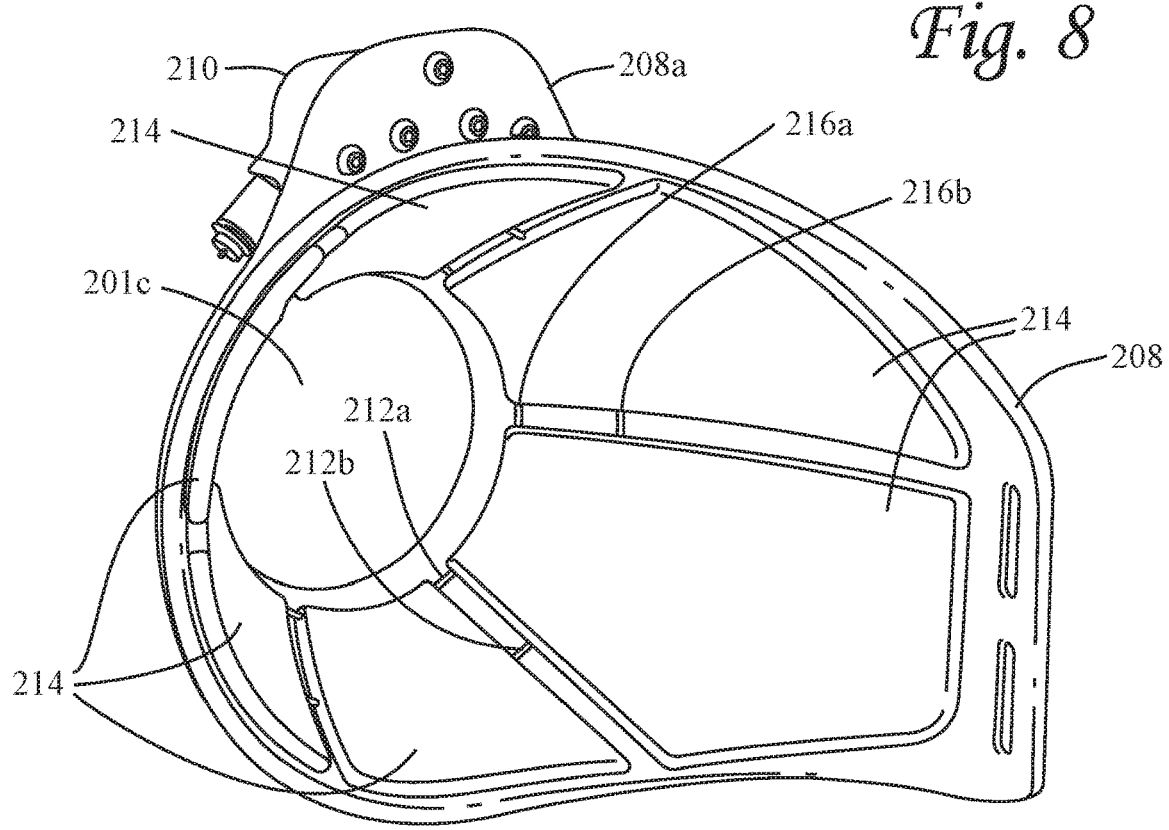
FIG. 8 shows a view of the breast milk expression apparatus of FIG. 7 from an inner side thereof.
Figure 9:
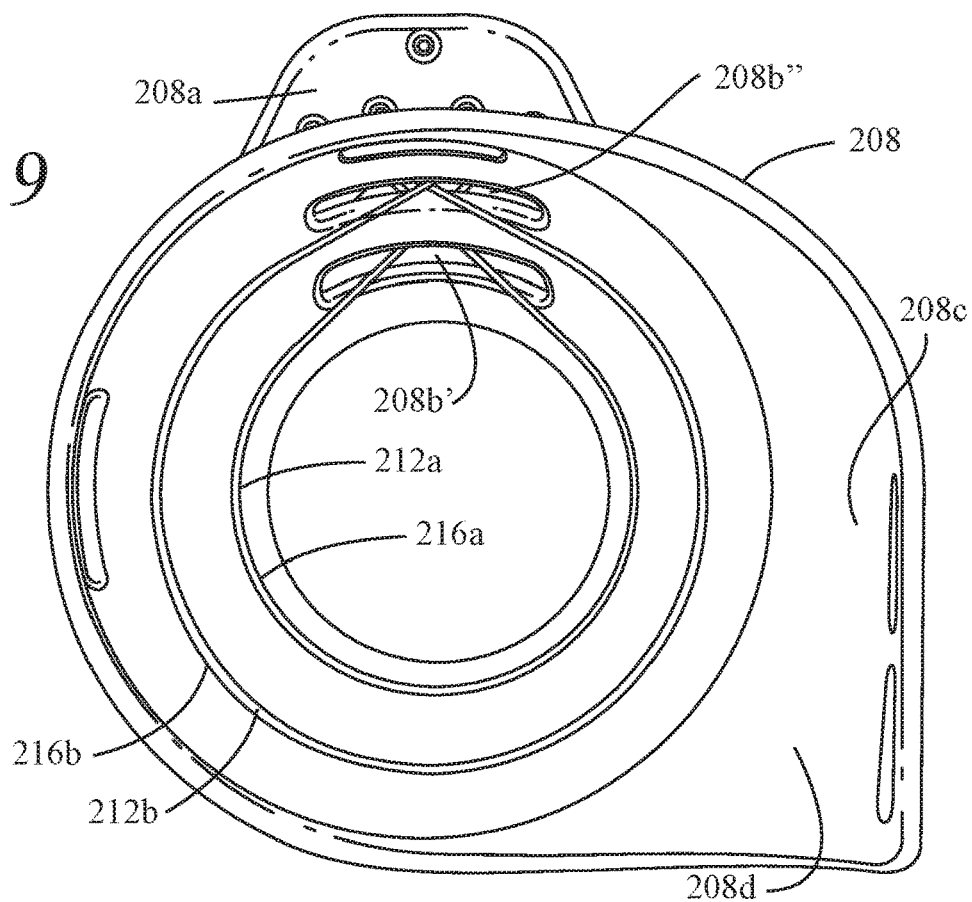
FIG. 9 shows the breast milk expression apparatus of FIG. 8 with pads removed therefrom to show details of an outer shell of the breast milk expression apparatus.
Figure 10:
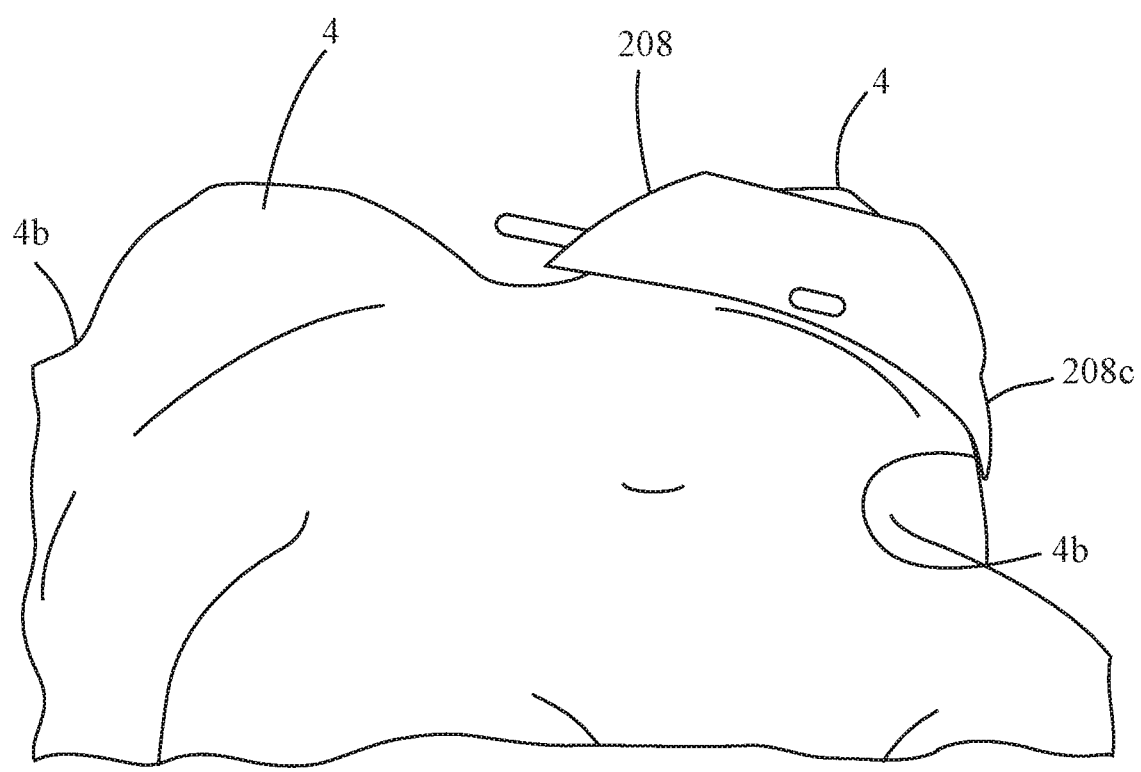
FIG. 10 shows the breast milk expression apparatus of FIG. 7 positioned on a breast.

An example of an embodiment of an expression apparatus 201 having multiple cable channels, grooves, and cables is shown in FIGS. 7 to 9. The expression apparatus 201 has the same function as the expression apparatus 1, but differs in structure in that the expression apparatus 201 includes a plurality of cable channels, grooves, and cables, further details of which are provided below. In the embodiment of the expression apparatus 201, elements corresponding to expression apparatus 1 are incremented by "200". Thus, as shown in FIG. 7, the expression apparatus 201 has an outer shell 208 with a deck 208a that supports a drive unit 210.

As shown in FIG. 8, the expression apparatus 201 has a plurality of pads 214 on an inner side of the outer shell 208. The pads 214 have a plurality of channels 216a and 216b through which corresponding cables 212a and 212b extend. For each pad 214, channel 216a is spaced from channel 216b, and channel 216a is located closer to opening 201c in the expression apparatus 201 than channel 216b.

Figure 7A:
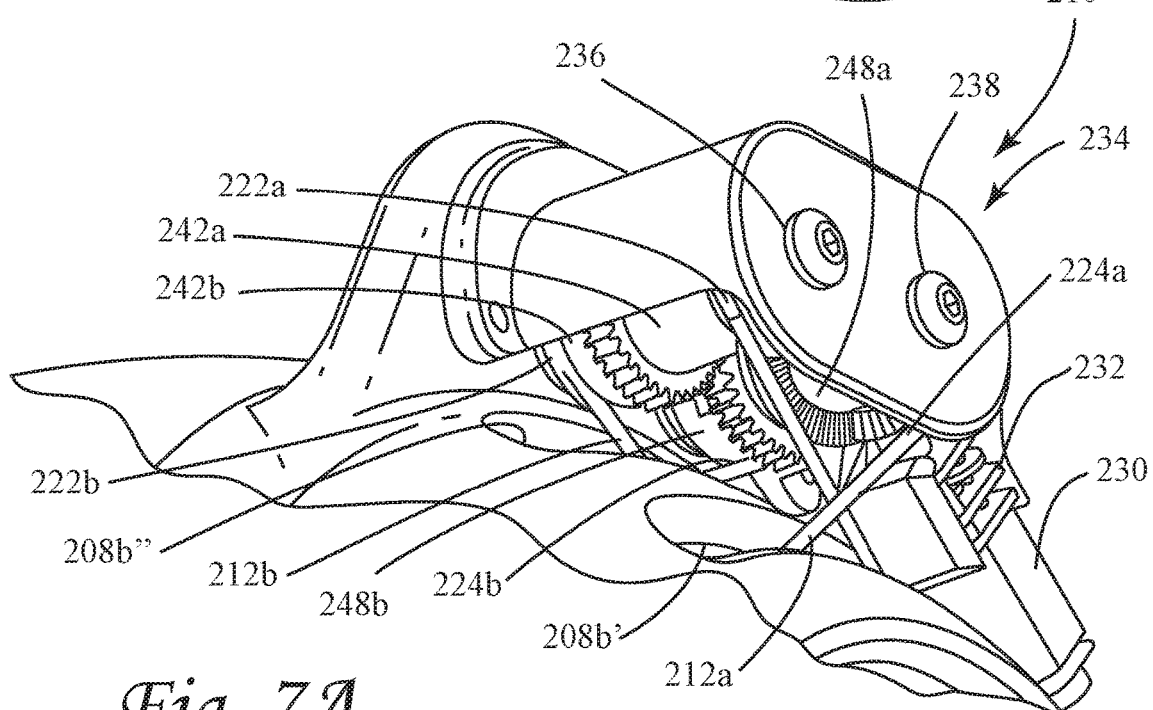
FIG. 7A shows an exploded view of a portion of the breast milk expression apparatus of FIG. 7.

The outer shell 208a defines openings 208b' and 208b" through which corresponding cables 212a and 212b extend, as shown in FIGS. 7, 7A, and 9. As shown in greatest detail in FIG. 7A, cable 212a has ends 222a and 224a that are routed to a transmission system 234 of the drive unit 210. The drive unit 210 includes an electric motor 230, a gearbox 232 driven by the motor 230, and the transmission system 234 driven by the motor 230. End 222a is routed to a pulley 242a on shaft 236 of the transmission system 234 and end 224a is routed to a pulley 248a on shaft 238 of the transmission system 234. The other cable 212b has ends 222b and 224b that are routed to the transmission system 234 of the drive unit 210. Specifically, end 222b is routed to a pulley 242b on shaft 236 and end 224b is routed to a pulley 248b on shaft 238. The shafts 236 and 238 correspond to shafts 36 and 38 of drive unit 10 and shafts 236 and 238 are coupled together and driven by a geared arrangement in the same manner as shafts 36 and 38. Thus, a detailed description of the drive unit 210 and its operation in driving shafts 236 and 238 with the motor 230 and gearbox 232 is omitted for brevity. As noted above, the operation of the expression apparatus 201 is the same as for expression apparatus 1. When the drive unit 210 is operating in one direction, it tensions both of the cables 212a and 212b around the pads 214 to compress the breast. When the drive unit 210 reverses direction, cables 212a and 212b loosen (relax) and permit the breast to decompress.

Figure 11A:
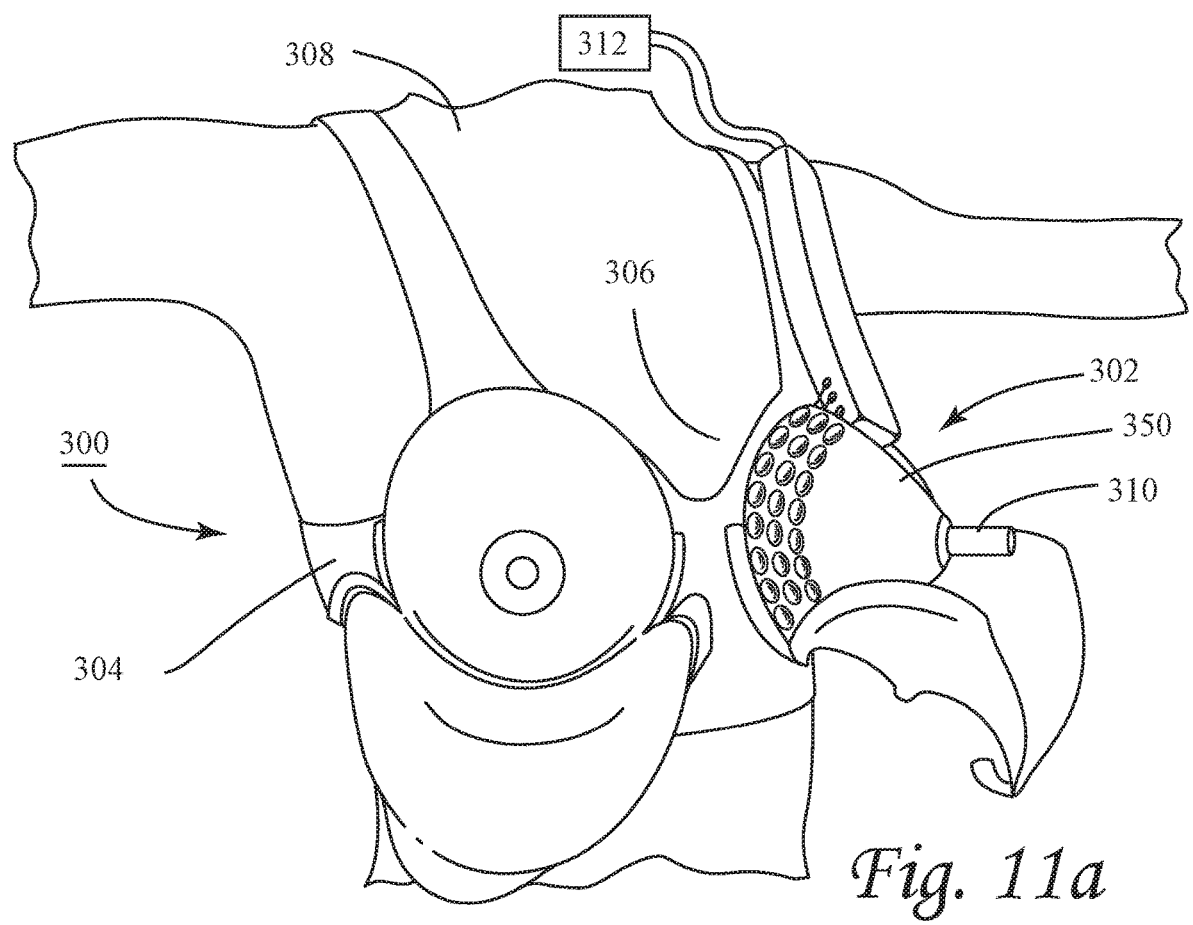
FIG. 11a is a front view of another embodiment of a breast milk expression system.
Figure 11B:
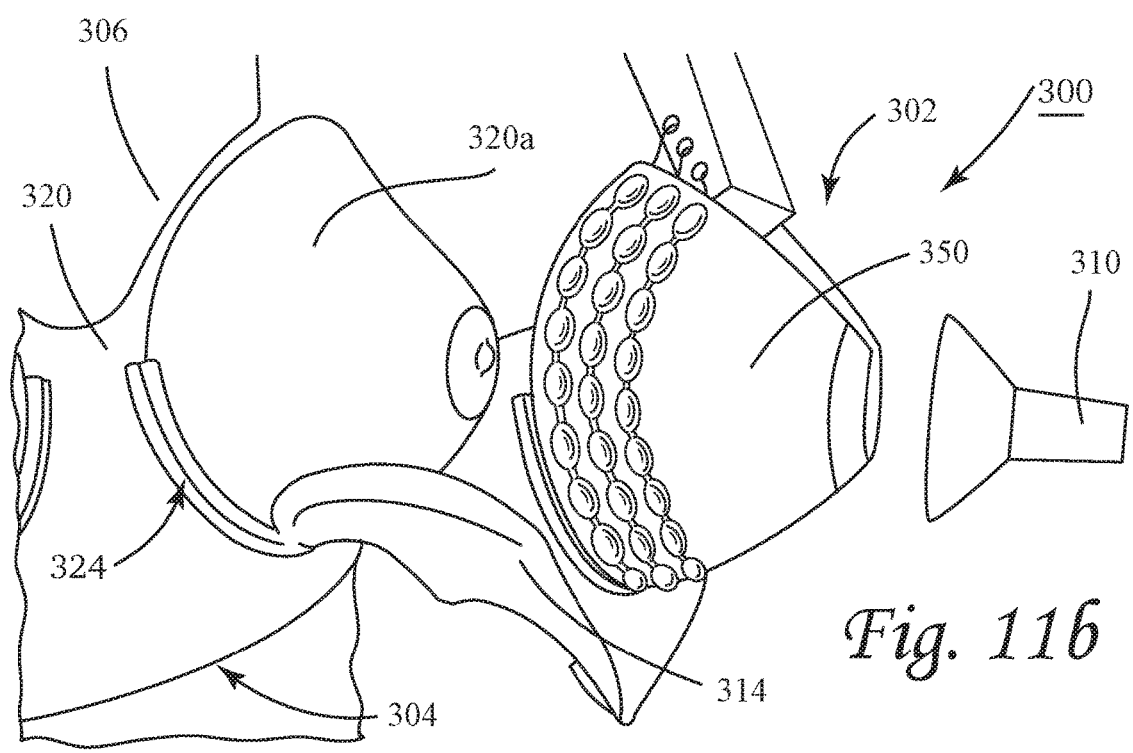

FIGS. 11a and 11b show another embodiment of a breast milk expression system 300. The system 300 includes a breast milk expression apparatus 302 and a nursing-style bra 304 which is removably connected to the breast milk expression apparatus 302. The breast milk expression apparatus 302 includes a compression pad 350 that is configured to squeeze a breast of a user 308 to perform breast milk expression. The bra 304 is configured to hold the breast milk expression apparatus 302, and specifically the compression pad 350, in fixed relation with respect to the user's breast 306. As will be appreciated, a breastshield 310 can be used with the system 300 and may be located between an inner cup 320a (e.g., inner surface of inner cup 320a) of the bra 304 and compressive pad 350. Preferably, the bra 304 is connected to the breast milk expression apparatus 302 and the system 300 is used like a bra, but also facilitates hands-free operation of one or two (if present) of the expression apparatuses 302. Each expression apparatus 302 (only one expression apparatus 302 is shown in FIGS. 11a and 11b) is configured to manipulate the tissue of the corresponding breast 306 based on a control input from a controller 312 (FIG. 11a), as described in greater detail below. The milk expression system 300 can be used before, during, and/or after breast pumping or nursing to facilitate lactation and improve milk production and flow. Further details of the breast milk expression system 300 and its operation will now be described.

FIGS. 12a to 12d show details of an embodiment of the bra 304 of the system. In the embodiment, the bra 304 is formed as a nursing-style bra with an outer layer 314 having folding cups 314a, an inner layer 320 (FIG. 12b) configured to be in contact with the breast 306, and adjustable shoulder straps 316. The bra 304 may come in various sizes based on the breast size of the user 308. The straps 316 are adjustable in length and are configured to support one or two expression apparatuses 302 over respective breasts 306 without the user 308 holding the expression apparatuses 302 in place, regardless of whether the expression apparatuses 302 are turned on or off.

Figure 12A:
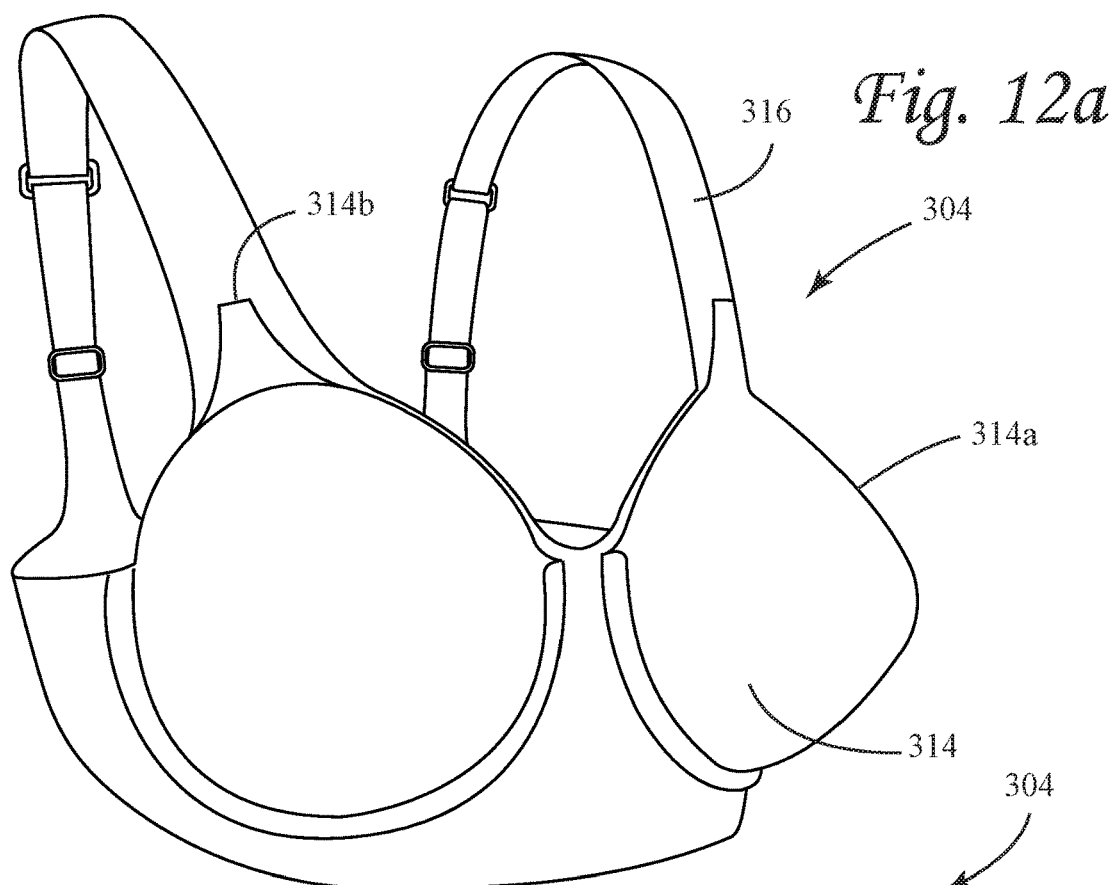
Figure 12B:
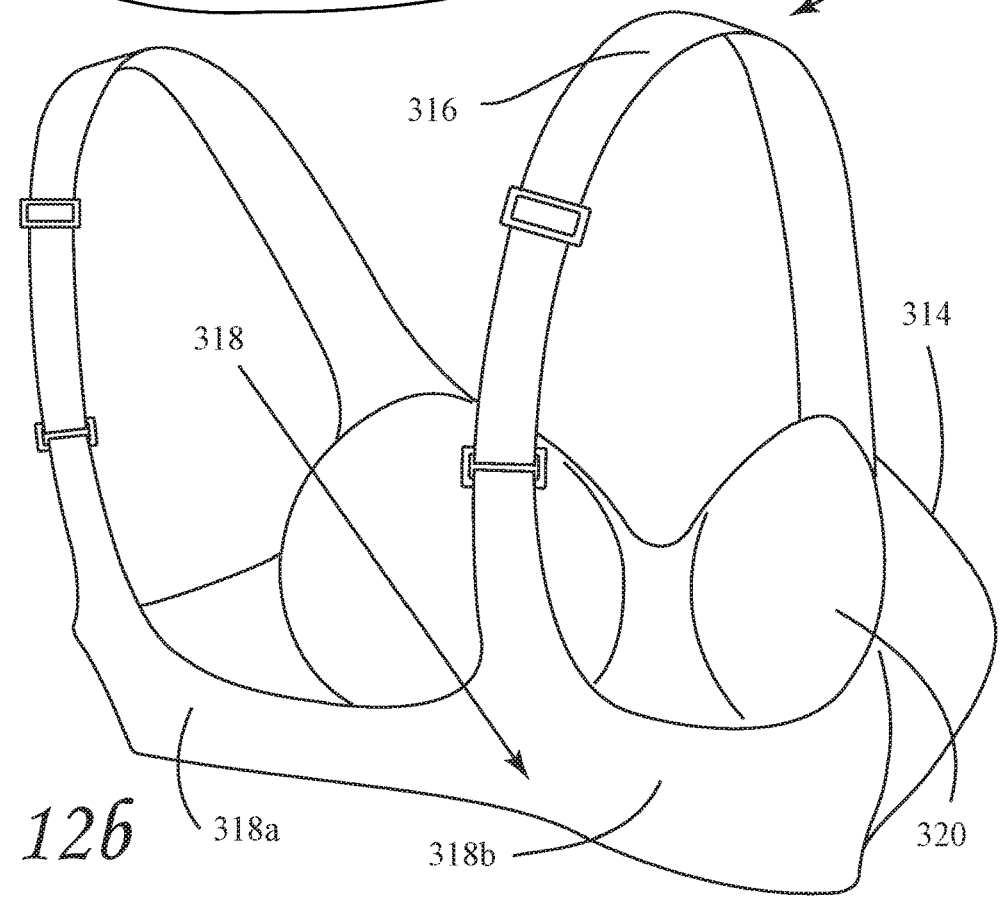
FIG. 12b shows the bra of FIG. 12a from the rear and a side.

As shown in FIG. 12b, at the back of the bra 304, the straps 316 connect to a corresponding back strap 318, which may be adjustable in length. The back strap 318 may be continuous or may be formed of segments. For example, in one embodiment, the back strap 318 is formed of a left segment 318a and a right segment 318b that are selectively connected in the middle of the strap with a suitable connector (not shown), which may permit adjustment of the length of the back strap 318.

Figure 12C:
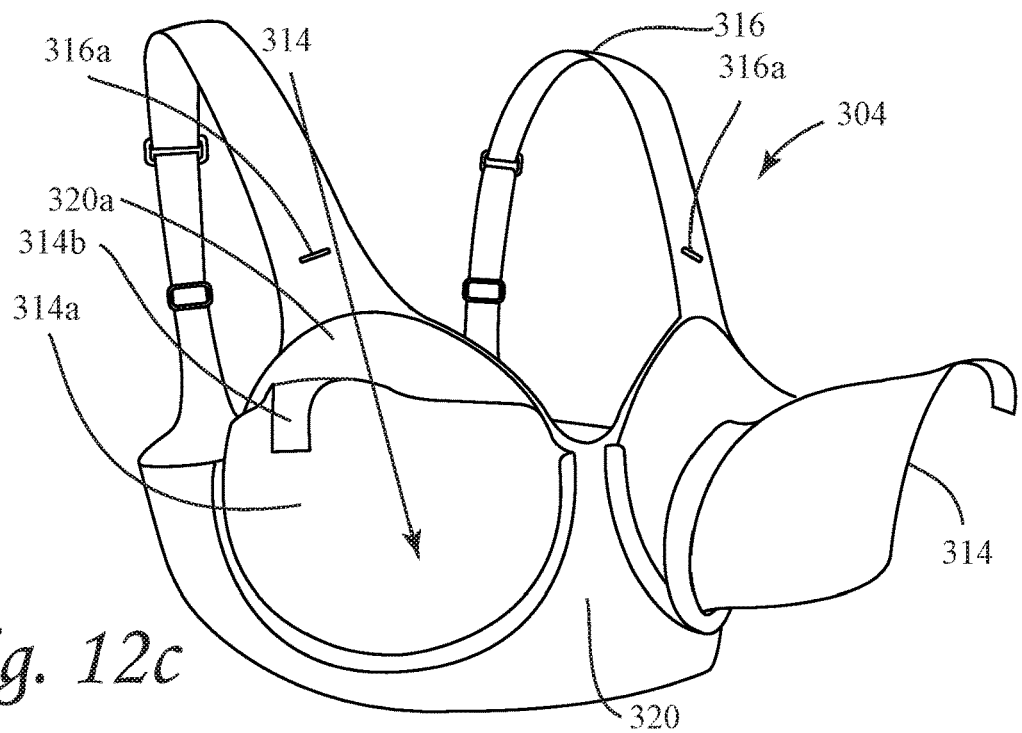
FIG. 12c shows the bra of FIGS. 12a and 12b with cups partially folded down.
Figure 12D:
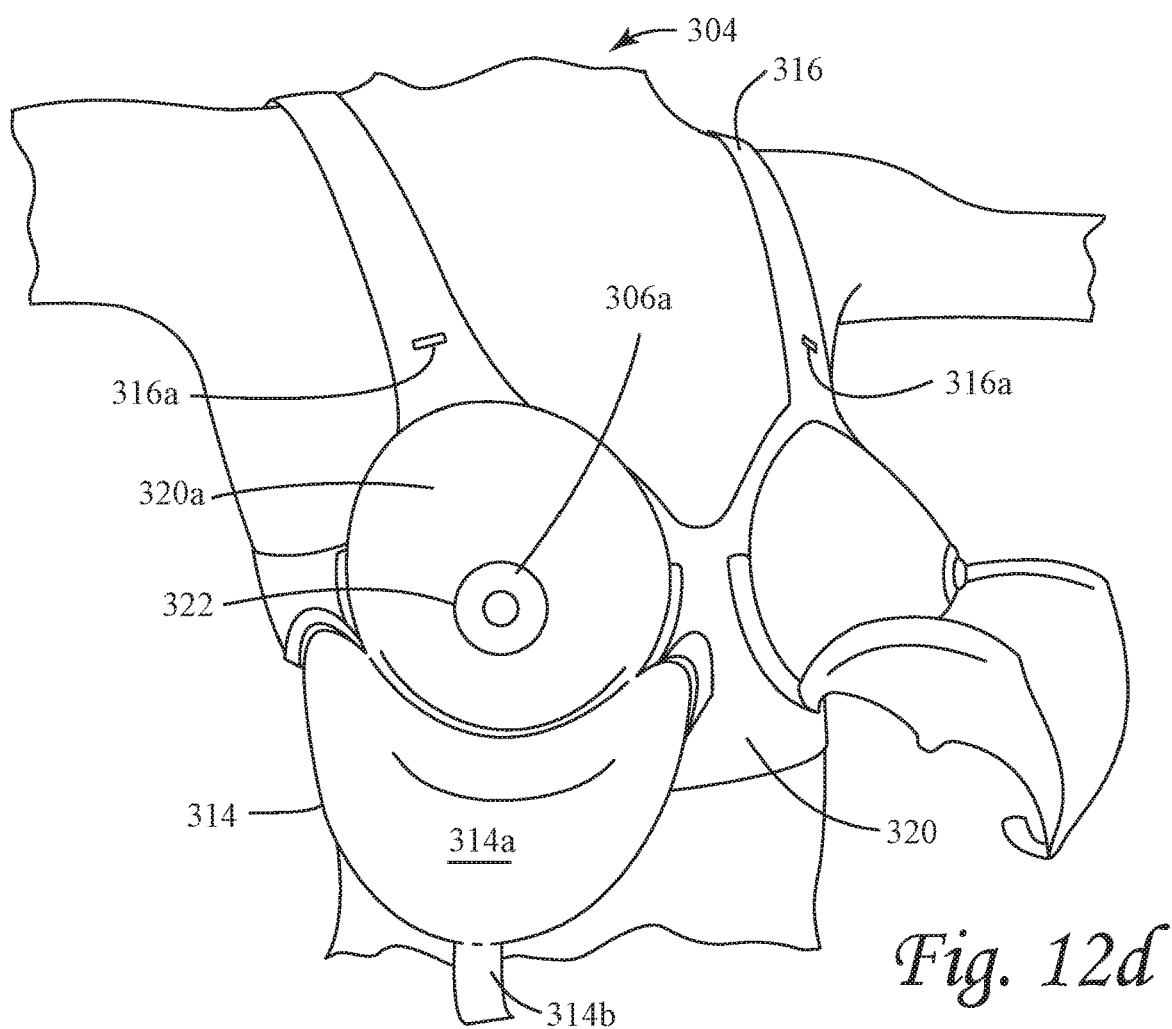
FIG. 12d is a front and side view of the bra shown in FIG. 1c with the cups folded further down.

As shown in FIGS. 12c and 12d, the cups 314a are configured as portions of the outer layer 314 of the bra 304 and can fold down independently of one another to expose respective inner cups 320a formed in the inner layer 320 of the bra 304. Each inner cup 320a, which may also be independently foldable, defines a hole 322 (FIG. 12d) located around a nipple area 306a (FIG. 12d) of the breast 306. Each inner cup 320a may have a removable connector 320b (FIG. 13c) (e.g., a snap connector, hook, or loop) at its upper end and a connector (e.g., stitching) at its bottom. The upper connector 320b may be removably connected to a connector 316b (FIG. 13c) (e.g., a snap connector, hook, or loop) on the strap 316. Such an arrangement may permit a user to disconnect the inner cup 320a at the upper connector and fold the inner cup 320a about the lower connector to permit the user to access the breast tissue, and specifically the nipple area 306a, for positioning the breastshield 310 thereon. The hole 322 is configured and sized so that a tubular part of the breastshield 310 (FIG. 11b) can extend through the hole 322 while a conical flange part of the breastshield 310 can be retained in engagement with the nipple area 306a between the inner cup 320a of the inner layer 320 and the nipple area 306a (i.e., in contact with the nipple area 306a).

Also, as shown in FIGS. 12c and 12d, each outer cup 314a may have a tab 314b that removably connects to a portion 316a of the strap 316. The connection between the tab 314b and the portion 316a may be a hook and loop connection, snap fit, and the like which allow the outer cup 314a to remain in place covering the inner cup 320a and the breast 306 or allow the cup 314a to fold away when so desired.

Figure 13A:
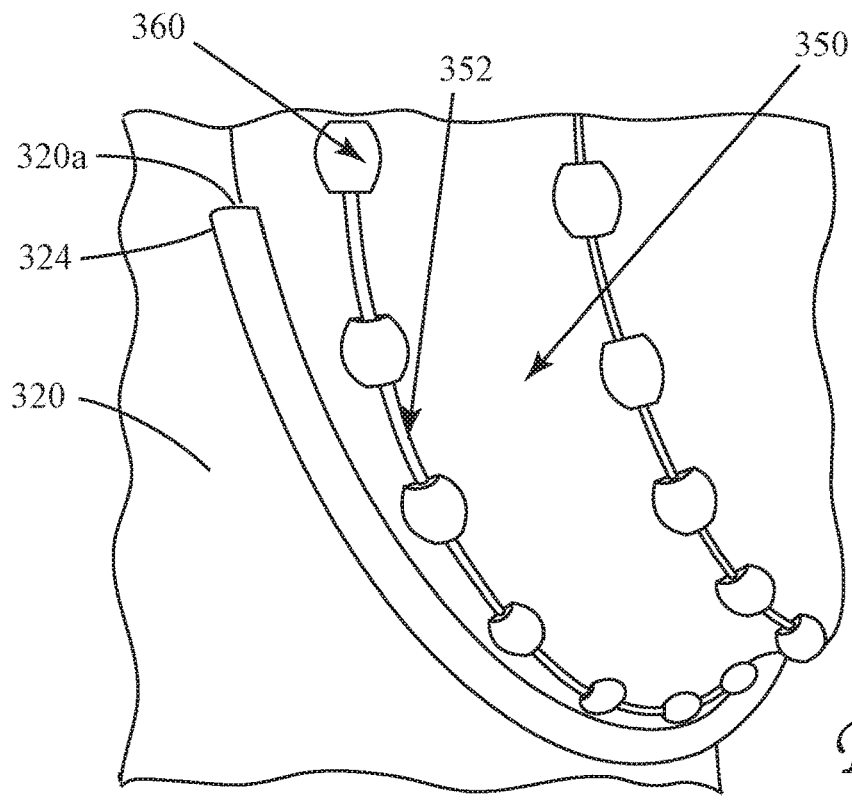
FIGS. 13a and 13b show details of one connection arrangement for connecting a compression pad of the breast milk expression apparatus shown in FIGS. 11a and 11b to the bra shown in FIGS. 11a, 11b, and 12a to 12d.
Figure 13B:
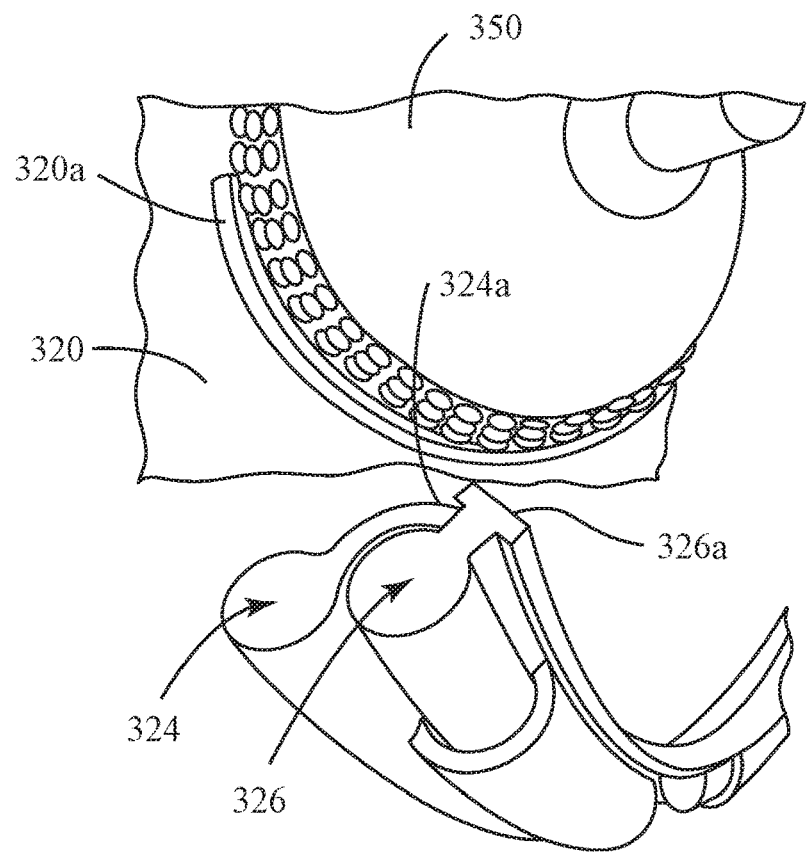

The expression apparatus 302 is configured to removably connect to the bra 304. One embodiment of a connection is shown in FIGS. 13a and 13b. As shown in FIGS. 13a and 13b, an attachment channel 324 is connected to (e.g., sewn to) the inner layer 320 and extends about the bottom at the base of the inner cup 320a of the inner layer 320, as shown with momentary reference to FIG. 11b. The attachment channel 324 is configured to mate with a corresponding channel 326 (FIG. 13b) affixed to the expression apparatus 302. In the embodiment shown in FIG. 13b, the channel 324 has a female circular profile with a slot 324a and the channel 326 has a male, solid circular profile with a "T" shaped portion 326a extending through the slot 324a. The "T" shaped portion 326a is fixed to the pad 350, e.g., sewn connection or adhesive.

Figure 13C:
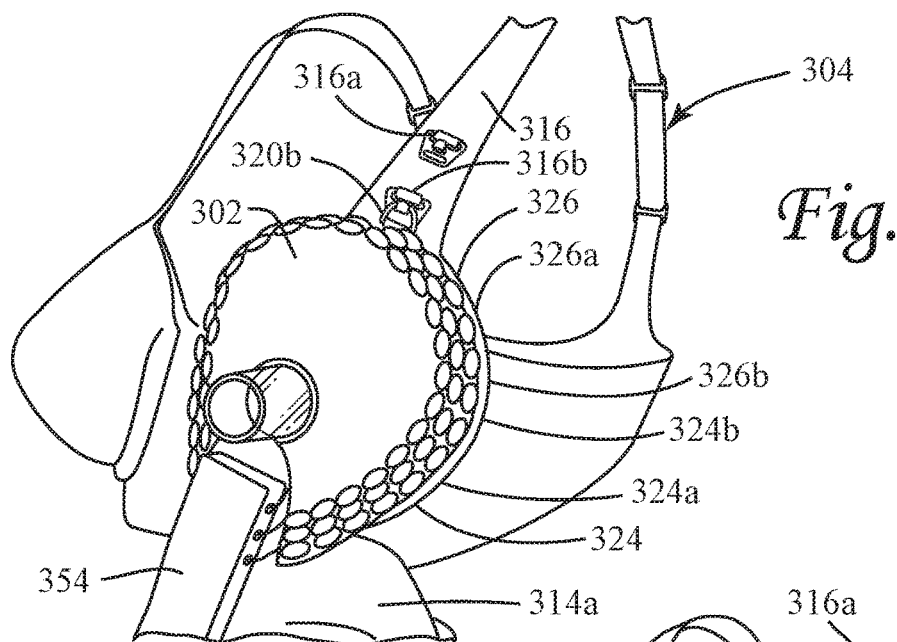
FIGS. 13c to 13e show details of a sequence of attaching the expression apparatus of FIG. 11a to the bra shown in FIGS. 11a, 11b, and 12a to 12d using the connection arrangement shown in FIGS. 13a and 13b.
Figure 13D:
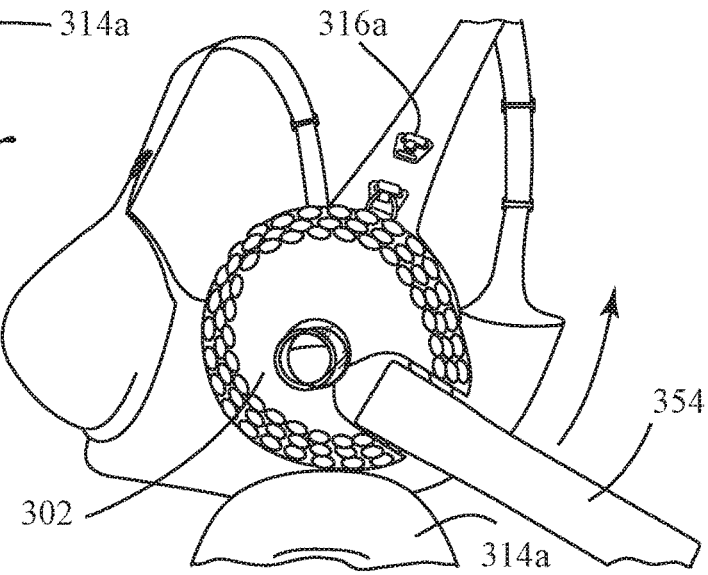
Figure 13E:
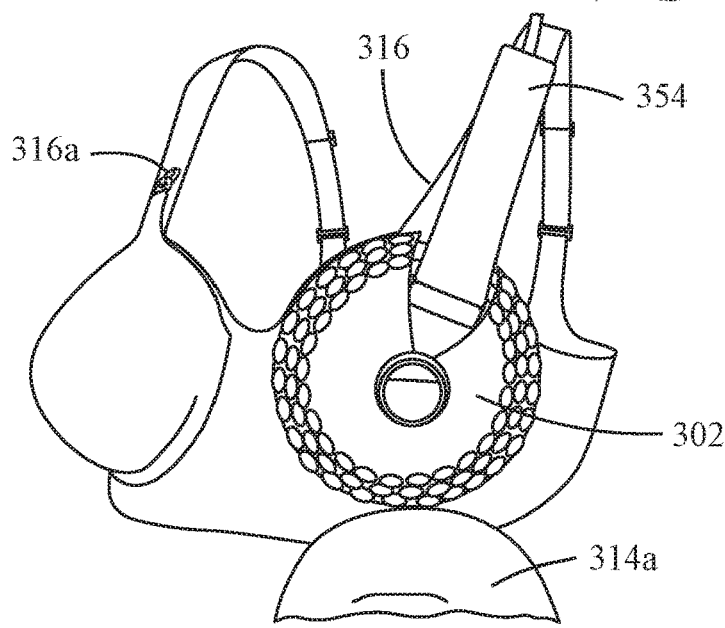

FIGS. 13c to 13e show a sequence for attaching the expression apparatus 302 to the bra 304 using the attachment channel 324 and the channel 326. As shown in FIG. 13c, the attachment channel 324 and the channel 326 are substantially semicircular and a user can position the expression apparatus 302 such that the channel 326 is aligned above the attachment channel 324 so that the attachment channel 324 and the channel 326 form a substantially circular pattern. Specifically, in FIG. 13c, ends 324b of slot 324a are aligned with respective ends 326b of the T-shaped portion 326a on both left and right sides of the expression apparatus 302, though only the right side is shown in FIG. 13c. Also, in FIG. 13c, a routing module 354 (described in greater detail below), extends downwardly from the expression apparatus 302. With the ends 324b and 326b aligned, the expression apparatus 302 can be rotated in the direction of the arrow (e.g. counter-clockwise) of FIG. 13d to further engage the attachment channel 324 and the channel 326. The expression apparatus 302 is rotated until the channel 326 is received and extends fully within the attachment channel 324 and the routing module 354 extends substantially in alignment with shoulder strap 316 (as seen in FIG. 13e), whereupon the routing module 354 may be removably attached to the strap 316 with suitable connectors, which may attach to connection 316a (FIGS. 13d and 13e), for example.

Figure 14:
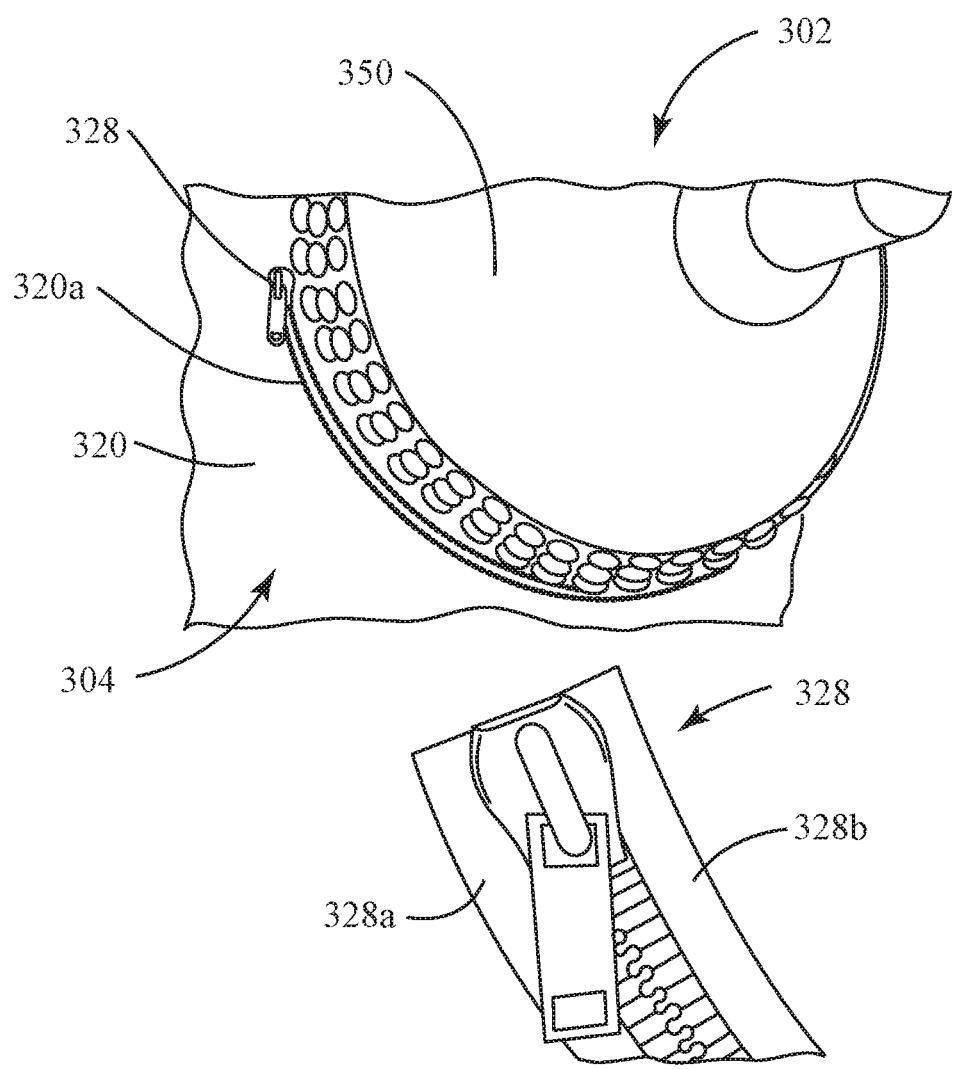
FIG. 14 shows details of another connection arrangement for connecting a compression pad of the breast milk expression apparatus shown in FIGS. 11a and 11b to the bra shown in FIGS. 11a, 11b, and 12a to 12d.

A second embodiment of a connection between the expression apparatus 302 and the bra 304 is shown in FIG. 14, which shows a zipper 328 used as the connection. Specifically, one half 328a of the zipper 328 extends along a lower half of the inner cup 320a of the inner layer 320 and another half 328b is connected around (e.g. sewn to) a lower portion of the expression apparatus 302. The halves 328a and 328b are configured to mesh or zip together to connect the expression apparatus 302 to the bra 304 and the halves 328a and 328b are configured to unmesh or unzip to disconnect the expression apparatus 302 from the bra 304. In one aspect, other means of attachment such as clips, or hooks and loops (e.g., Velcro) may be utilized.

Figure 19A:
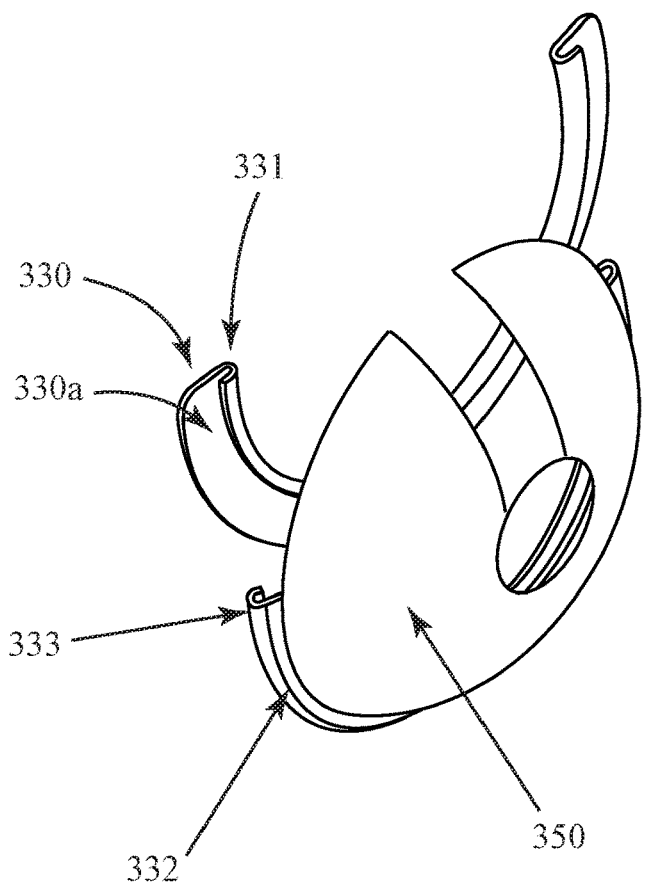
FIGS. 19a to 19c shows details of another connection arrangement for connecting a compression pad of the breast milk expression apparatus shown in FIGS. 11a and 11b to the bra shown in FIGS. 11a, 11b, and 12a to 12d.
Figure 19B:
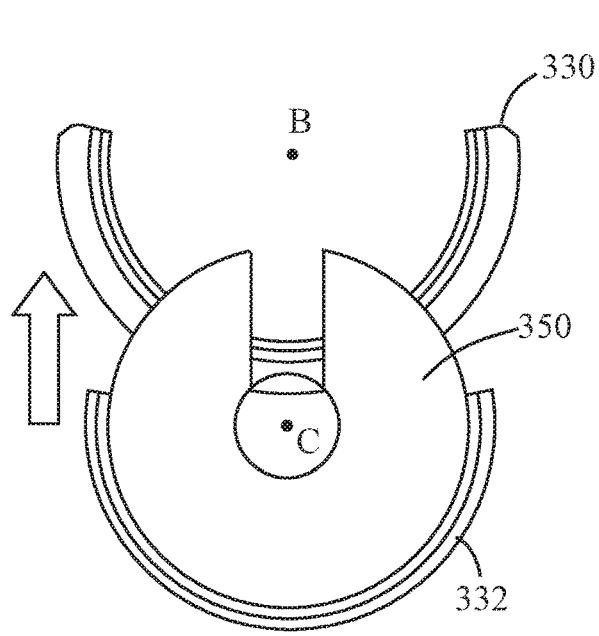
Figure 19C:
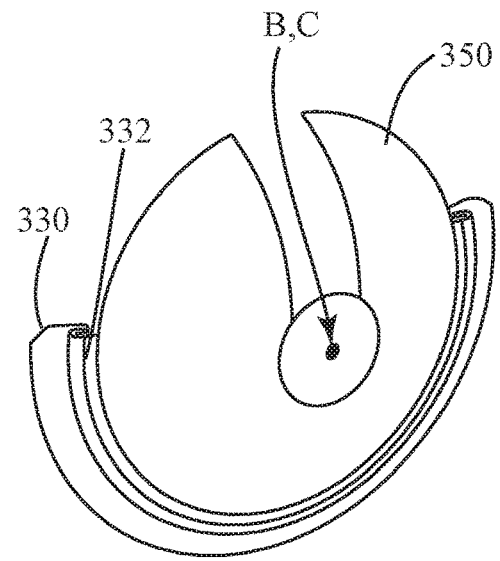

A third embodiment of a connection between the expression apparatus 302 and the bra 304 is shown in FIGS. 19a to 19c, which shows a first hook 330 having a female channel 331 and a second hook 332 having a male channel 333. The first hook 330 has a flange 330a which can be securely fastened to the inner layer 320 under the inner cup 320a. The second hook 332 extends around the lower half of the compression pad 350. The first hook 330 and the second hook 332 extend circumferentially about respective axes B and C, as shown in FIG. 19b. The female channel 331 and the male channel 333 are configured to slide into engagement as shown in FIG. 19b in the direction of the arrow so that the axes B and C come into alignment when the first hook 330 and the second hook 332 are fully connected, as shown in FIG. 19c. A diameter of the second hook 332 is slightly smaller than a diameter of the first hook 330 to permit the second hook 332 to expand slightly and snap onto the first hook 330 when the second hook 332 is slid upwardly in the direction of the arrow shown in FIG. 19b. Although the routing module 354 in FIGS. 13c to 13e is not shown in FIGS. 19a to 19c for clarity of illustration, the module 354 may be present and connected to pad 350 in FIGS. 19a to 19c and the module 354 may be connected to strap 316 of bra 304. Such connection of the module 354 to the strap 316 may be useful for providing additional support to the pad 350 to prevent disconnection of the second hook 332 from the first hook 330 due to the weight of the pad 350.

It will be appreciated that the bra 304 may be connected to structures other than the expression apparatus 302. For example, heating pads and cooling pads can be configured to have connections like those shown in FIGS. 13a, 13b, and 14 to connect to the bra 304 to apply, respectively, heating or cooling to the breast 306. Also, the other structures may include medicated pads, which when connected to the bra, may be configured to deliver medication to the breast 306.

Figure 15:
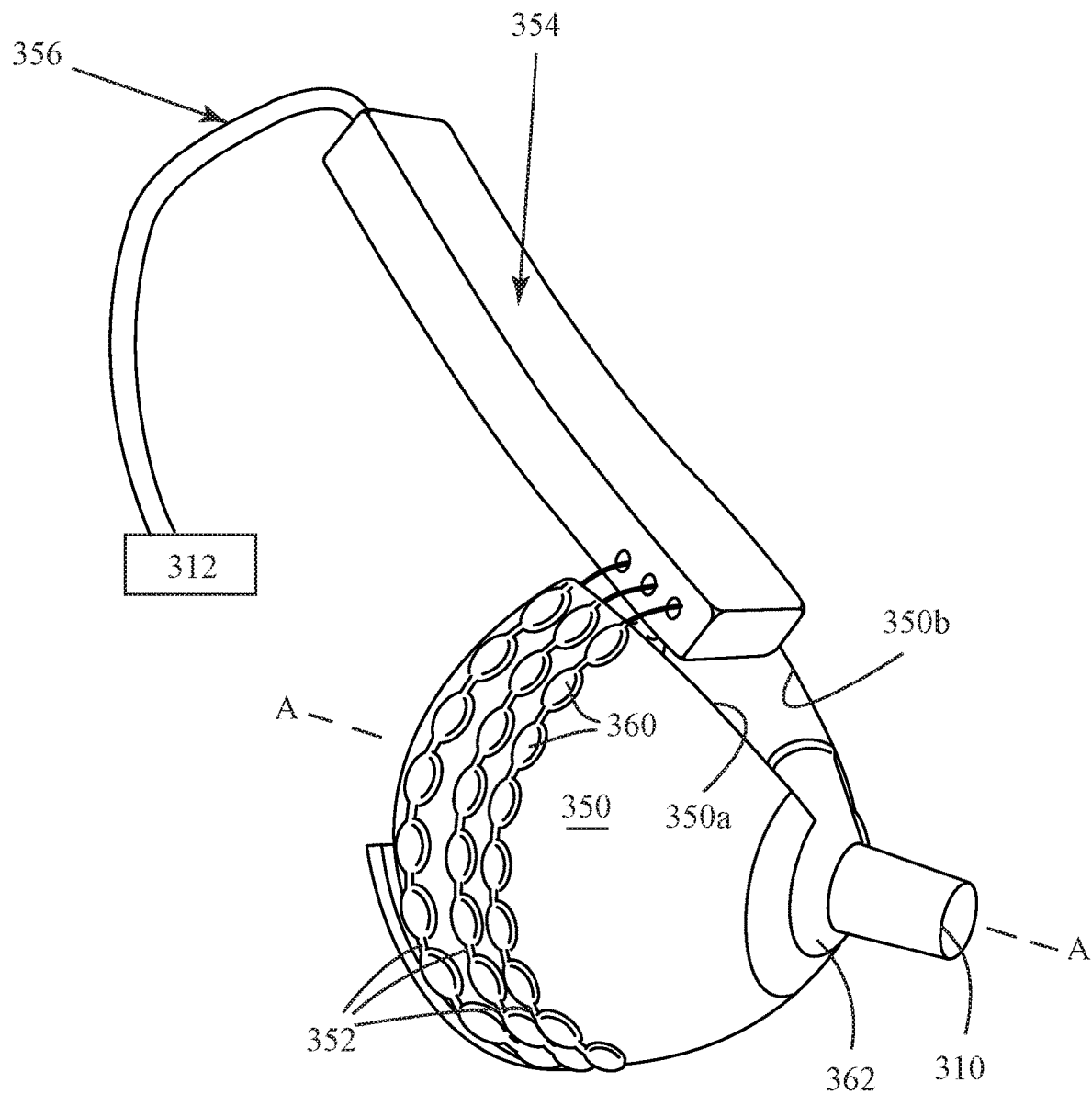
FIG. 15 shows a detailed view of the breast milk expression apparatus shown in FIGS. 11a and 11b.

FIG. 15 shows additional details of the expression apparatus 302. The expression apparatus 302 includes a compression pad 350 having a plurality of strings 352 arranged concentrically with axis A-A. For purposes herein, the term "string" is to be understood broadly to include monofilaments, multifilaments, twisted filaments, etc., which may be comprised of any of several materials such as metal, polymers which are substantially inelastic in tension, or other suitable materials, or combinations thereof. The expression apparatus 302 also includes a routing module 354 and a gearbox 312 (shown schematically) coupled to the strings 352. In one embodiment, each respective string 352 has one end that terminates in the module 354 and an opposite end that terminates in the gearbox 312. In another embodiment, each respective string 352 has two ends that terminate in the gearbox 312. In the embodiment shown in FIG. 15, the strings 352 are routed between the module 354 and the gearbox 312 by a tether 356. In another embodiment, instead of a single tether 356 routing all of the strings 352, a plurality of tethers may be used to individually route each string between the module 354 and the gearbox 312. It will be appreciated that in one embodiment, the gearbox 312 is integrated with the module 354 eliminating the tether 356. The tether 356 is preferably sufficiently long so as to permit the user 308 to dispose the gearbox 312 below the user's breast 306, and, preferably, proximate to a waist of the user 308. As will be described in greater detail below, the gearbox 312 is configured to pull on the strings 352 to radially compress the compression pad 350 and the breast 306 (e.g., via the inner cup 320a of the inner layer 320).

Each string 352 is routed through a corresponding plurality of circumferentially spaced beads 360, which are secured to the compression pad 350. Each string 352 is configured to slide freely through an opening defined in each bead 360. The beads 360 may have a flat outer surface, as illustrated in FIG. 15, or they may have other outer shapes, such as cylindrical and round (e.g., spherical). The beads 360 may be secured to the compression pad 350 with adhesive (e.g., glue) or with mechanical fasteners (e.g., by sewing) and may be secured either on the outer surface of the pad 350 or within channels (not shown) recessed into the outer surface of the pad 350. As an alternative to the beads 360, the strings 352 may be routed through tubular channels secured to the pad 350. Such tubular channels may be secured to the outer surface of the pad 350, or may be secured in recessed channels formed in the outer surface of the pad 350. Such tubular channels may be formed by sewing material (e.g., fabric) into a tube and connecting the tube to the pad 350. Also, the aforementioned tubular channels may be a single continuous channel or may be a plurality of tubular channels circumferentially spaced about axis A-A approximating the arrangements (e.g., number and spacing) of the beads 360 shown in FIG. 15. The strings 352 are axially spaced from one another along axis A-A.

The number and longitudinal spacing of the strings 352 may be determined based on at least one of the size of the breast 306 and the timing of a compression sequence, further details of which are described below. Also, the number and circumferential spacing of the beads 360 along each string 352 may be determined based on at least the size of the breast 306, with the either more beads being used at the same spacing for an expression apparatus accommodating a relatively larger breast, or the same number of beads being spaced further apart, or both.

The compression pad 350 may be made from fabric, polymer, or any flexible material. The compression pad 350 defines a hole 362 at a distal end corresponding to the nipple area 306a (FIG. 12d) and aligned with the hole 322 (FIG. 12d) in inner cup 320a (FIG. 12d). The hole 362 is configured to receive therethrough a portion of the breast shield 310, as shown in FIG. 15.

The compression pad 350 has an outer surface that is substantially tapered (e.g., frustoconical or convex) along axis A-A and which is substantially (at least 75%) continuous about axis A-A. In the embodiment shown in FIG. 15, the pad 350 is discontinuous about axis A-A and extends from one end 350a to an opposite end 350b. The module 354 is disposed in spaced relation to and between the ends 350a and 350b of the compression pad 350 so that the module 354 directly contacts the inner cup 320a (FIG. 11b) of the inner layer 320 (FIG. 11b). It will be appreciated, however, that the pad 350, in at least one other embodiment, may be circumferentially continuous and extend 360 degrees around axis A-A.

Figure 16A:
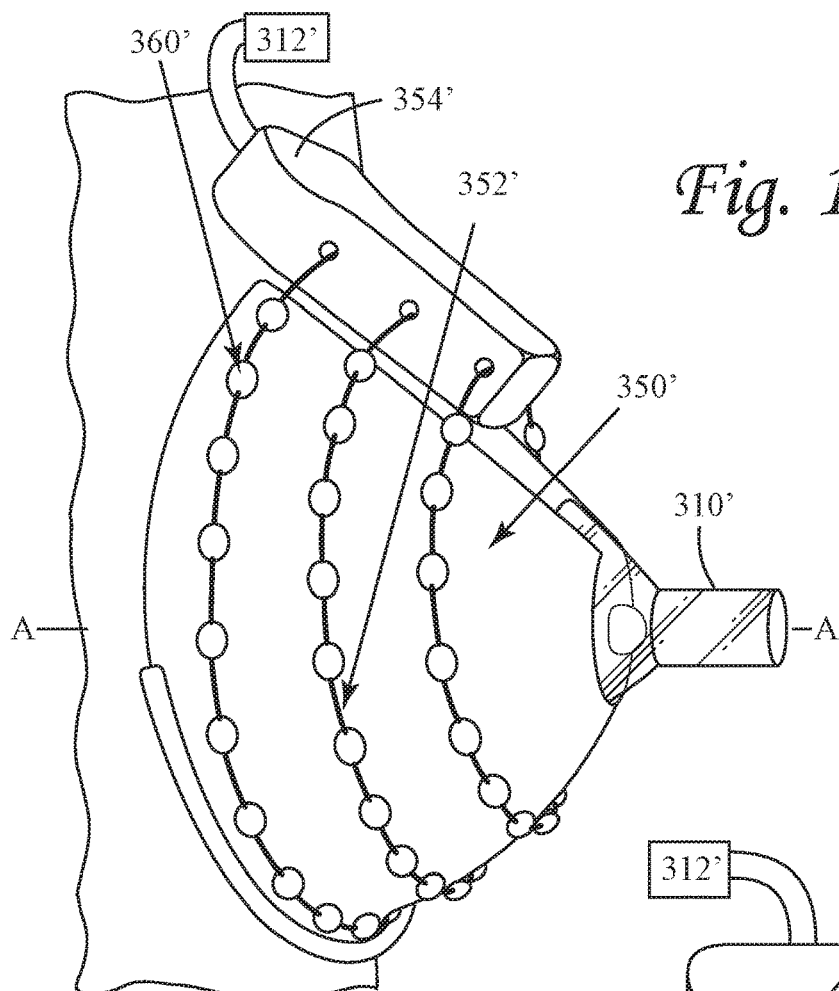
FIG. 16a shows a side view of another embodiment of the breast milk expression apparatus.
Figure 16B:
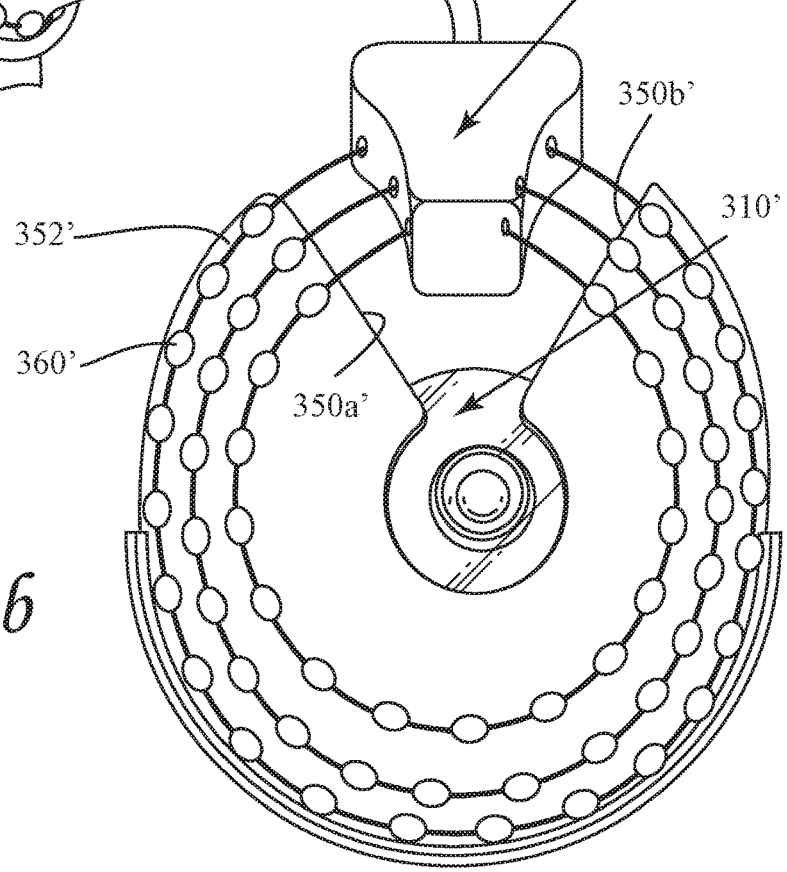

FIGS. 16a and 16b show another embodiment of the expression apparatus 302' which is the same as expression apparatus 302 with the exception of routing module 354', which is shorter than module 354 and has curved sides instead of straight sides of slimmer module 354. In FIGS. 16a and 16, elements of the expression apparatus 302' that correspond to elements of the expression apparatus 302 are appended with an apostrophe (').

Figure 17A:
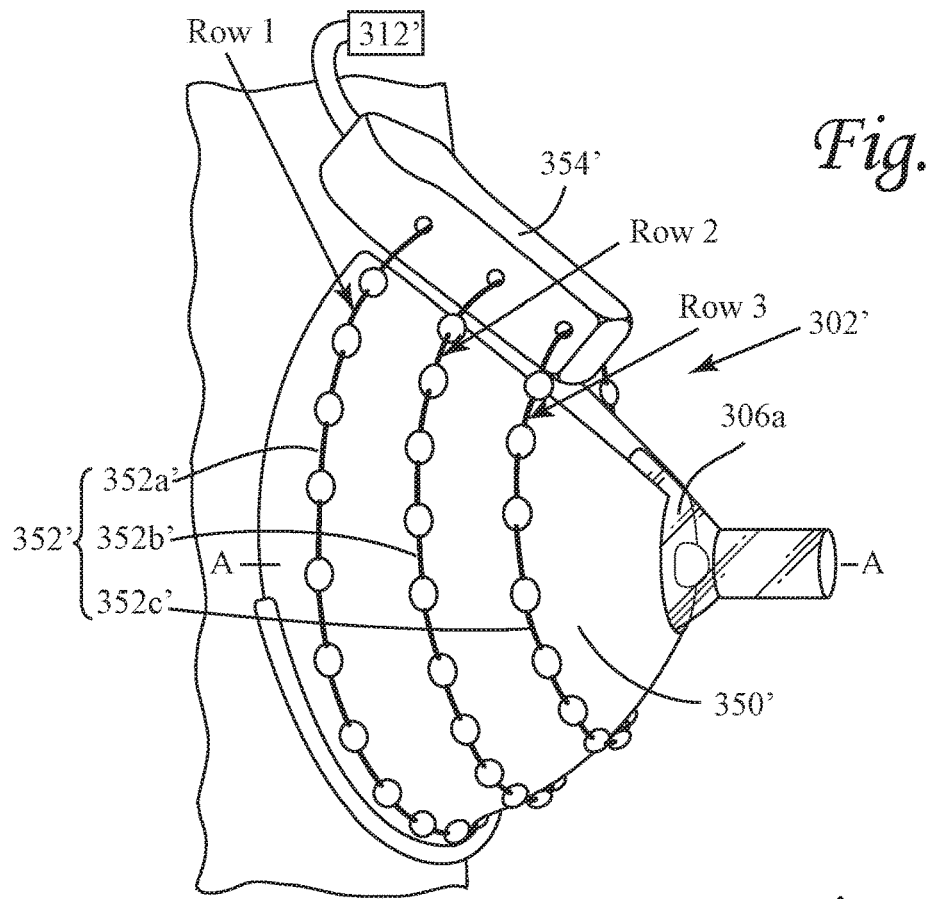
FIGS. 17a to 17c show details of the operation of the breast milk expression apparatus shown in FIGS. 16a and 16b.
Figure 17B:
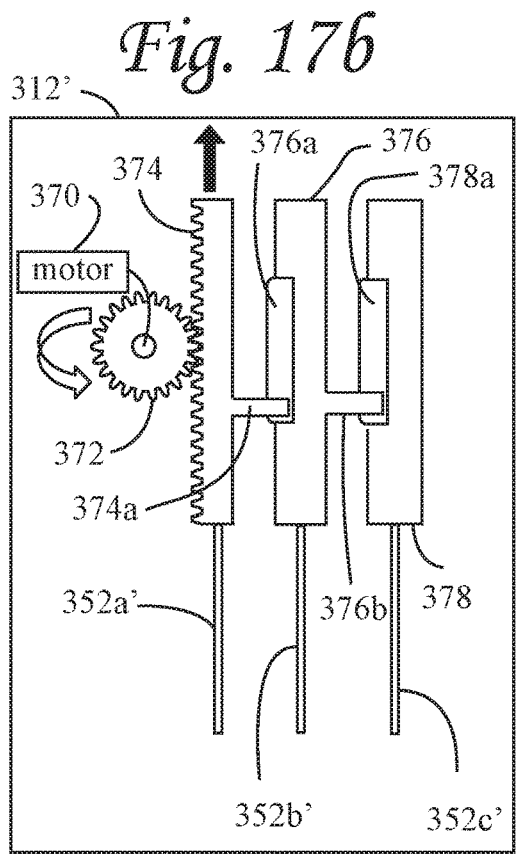
Figure 17C:
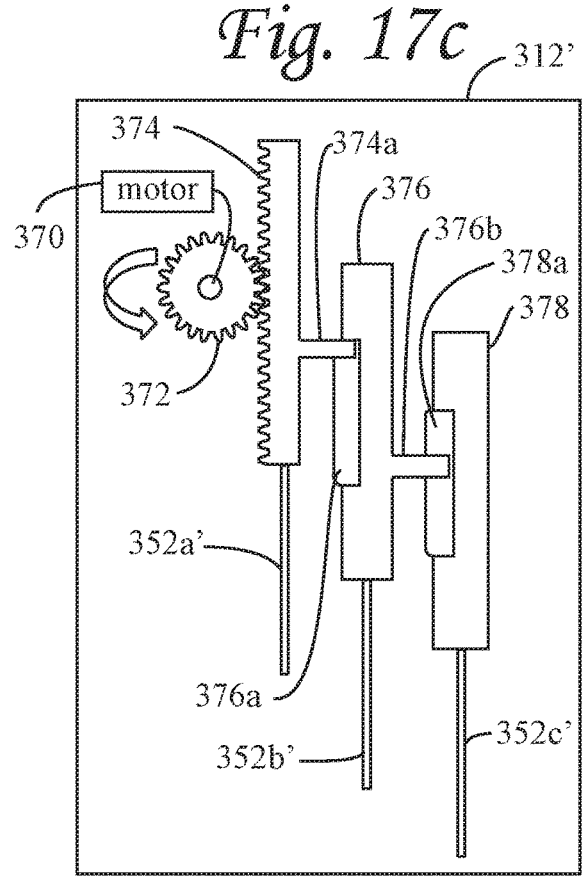

FIGS. 17a to 17c illustrate further details of the expression apparatus 302'. In FIGS. 17a to 17c, the plurality of strings 352' includes inner string 352a' (in relation to the torso of the user), middle string 352b', and outer string 352c' (being closest to the nipple area 306a along axis A-A). The gearbox 312' is configured to pull on respective ends of the strings 352a', 352b', and 352c' to concentrically tighten the respective strings around the pad 350', and, therefore, around the breast 306 to radially compress the breast 306. Specifically, with respect to the embodiment of the expression apparatus 302' shown in FIGS. 16a, 16b, and 17a, when one or more of the strings 352a', 352b', and 352c' are tightened by the gearbox 312' they compress the sides and underside of the breast 306 through the compression pad 350' and inner cup 320a (FIG. 11b) of the inner layer 320 (FIG. 11b), while the module 354' compresses the top of the breast 306 through the inner cup 320a (FIG. 11b). The module 354' may be shaped in various ways to cover more or less of the inner cup 320a (FIG. 11b).

In one embodiment, the gearbox 312' is configured to tighten the strings 352a', 352b', and 352c' in a compression sequence, one of which is described below with reference to FIGS. 17b and 17c. The gearbox 312' includes a motor 370 and a pinion gear 372 driven by the motor 370. The motor 370 may be powered by an electrical power source, such as an AC or DC power source, which may be internal or external from the gearbox 312'. In the gearbox 312' the end of inner string 352a' is connected to a rack 374 that is enmeshed with the pinion gear 372. The rack 374 and the inner string 352a' translate parallel to the length of the inner string 352a' (upwardly in FIGS. 17b and 17c) in the gearbox 312' when the pinion gear 372 rotates counter-clockwise. The end of the middle string 352b' is connected to a middle pull member 376 and the end of the outer string 352c' is connected to a pull member 378. The middle pull member 376 and the outer pull member 378 have respective elongated notches 376a and 378a defined along the length of the respective pull member. An engagement tab 374a extends to the right from the rack 374 into the elongated notch 376a of the middle pull member 376, and another engagement tab 376b extends from middle pull member 376 into the elongated notch 378a of the outer pull member 378.

The relative positions of the strings 352a', 352b', and 352c' shown in FIG. 17b is a neutral position in which all of the strings 352a', 352b', and 352c' are not in tension, corresponding to a position in which the breast 306 is not being compressed by the expression apparatus 302'. Whenever any of the rack 374, middle pull member 376, or pull member 378 is displaced (upward in FIGS. 17b and 17c) away from its respective neutral position, such displacement causes radial displacement of the compression pad 350 and compression of the breast 306 of the user 308. Owing to the arrangement of the notches 376a and 378a and the engagement members 374a and 376b, the timing of and sequence of moving each string 352a', 352b', and 352c' can be controlled during each upward stroke of the rack 374, corresponding to a compression phase of a compression-expansion cycle.

The operation of the gearbox 312' may be understood with reference to FIG. 17b and FIG. 17c. As the pinion gear 372 rotates counterclockwise in FIG. 17b, the rack 374 and engagement tab 374a translate upward until the engagement tab 374a engages the middle pull member 376 at the top of the elongated notch 376a, as shown in the position in FIG. 17c. Thereafter, continued counterclockwise rotation of the pinion gear 372 will cause both the rack 374 and the middle pull member 376 to move upwardly together until the engagement member 376b engages the outer pull member 378 at the top of the elongated notch 378a. Thereafter, continued counterclockwise rotation of the pinion gear 372 will cause the rack 374, middle pull member 376, and outer pull member 378 to move upward together until the rack 374 stops moving, thereby ending the upward compression stroke of the rack 374. Thereafter, the motor 370 can be temporarily turned off to begin an expansion stroke of the rack 374 and an expansion phase of the compression-expansion cycle upon which tension in the wires 352a', 352b' and 352c' is removed, allowing outward expansion forces exerted from the breast 306 to urge the strings 352a', 352b', and 352c' back to their neutral positions shown in FIG. 17b, completing the compression-expansion cycle. The compression-expansion cycle can be repeated multiple times to facilitate breast milk expression. Thus, based on the compression sequence, the inner string 352a' will compress the breast 306 first, followed by the middle string 352b', and lastly the outer string 352c', such that the breast 306 will be compressed progressively in an outward direction (longitudinal along axis A-A) from the base of the breast 306 toward the nipple area 306a (FIGS. 12d and 17a). Also, it will be appreciated that during each compression stroke of the rack 374, the string 352a' will be in tension for the longest period of time, followed by the middle string 352b', followed by the outer string 352c'.

While the gearbox 312' shown in FIGS. 17b and 17c is linear, the gearbox design may be circular or elliptical. Also, although not shown in FIGS. 17b and 17c, the gearbox 312' may be contained in a control box along with other electrical components for controlling the operation of the motor 370.

Figure 18A:
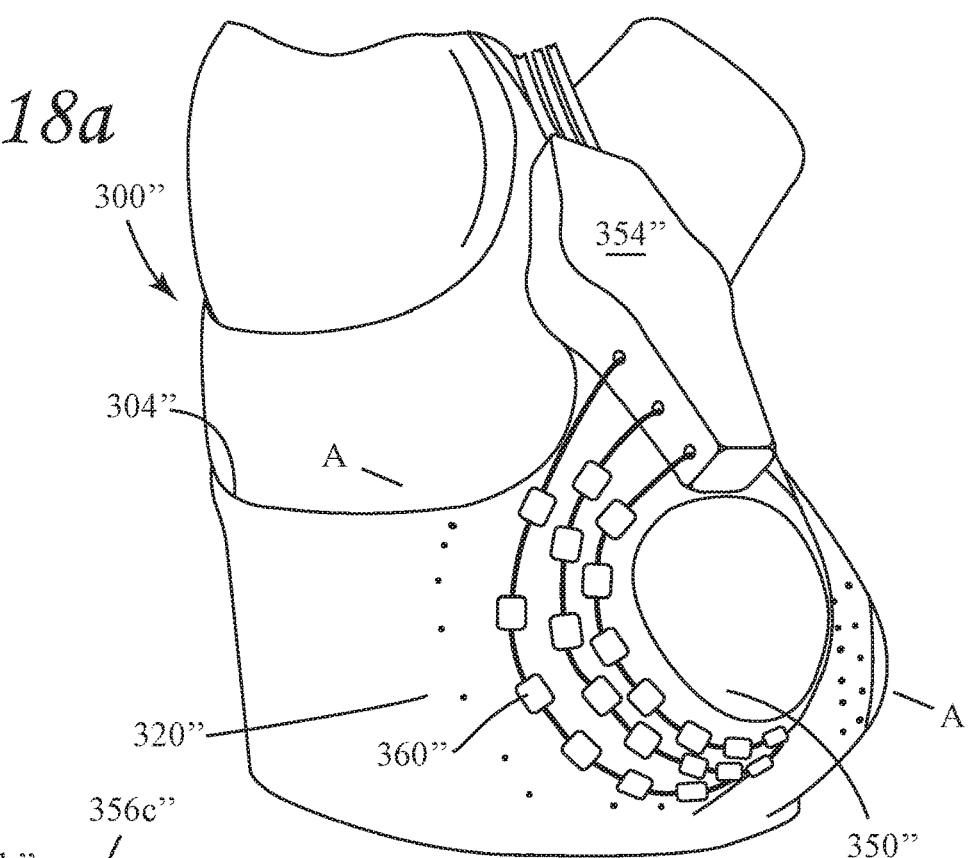
FIG. 18a shows another embodiment of a breast milk expression system.
Figure 18B:
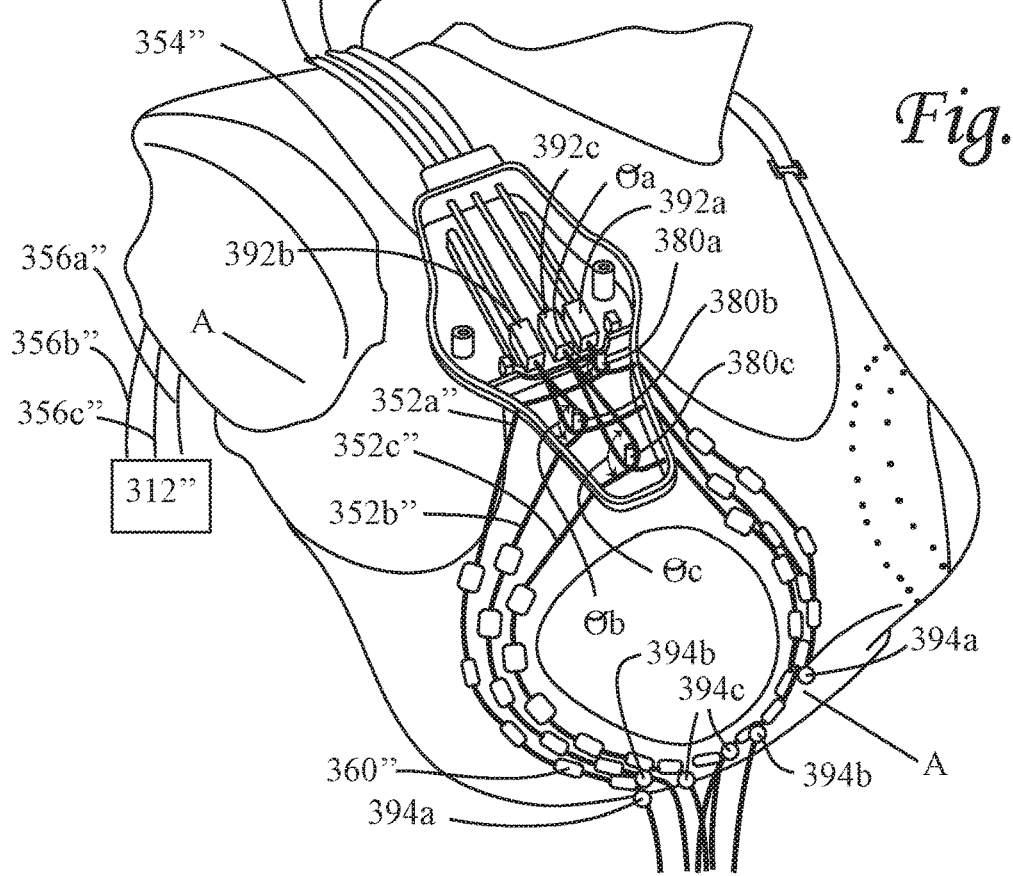
FIG. 18b shows the breast milk expression system of FIG. 18a with a cover of a module removed to show detail inside the module.

FIGS. 18a and 18b show an alternative embodiment of the system 300, and denoted 300". In FIGS. 18a and 18b elements of system 300" corresponding to those of system 300 are appended with two apostrophes (''). One notable difference between system 300" and system 300 is that the compression pad 350" is integrally formed with an inner layer 320" of a bra 304" and is not readily removable therefrom. Although not shown in FIGS. 18a and 18b, an outer layer may optionally be used to cover or enclose the compression pad(s) 350" and inner layer 320".

FIG. 18b shows another embodiment of a module 354" with an outer cover thereof (shown in FIG. 18a) removed to show a routing of three strings: string 352a", string 352b", and string 352c". The module 354" has three connection blocks 392a, 392b, and 392c, which are respectively connected to strings 352a", 352b", and 352c". Specifically, inside each connection block 392a, 392b, and 392c is a pin (not shown), around which respective strings 352a", 352b", and 352c" are looped. From connection block 392a, ends of string 352a" are routed around an upper pin 380a so that the string 352a" extends circumferentially around the compression pad 350". Ends of the string 352a" are formed into knots 392a adjacent to beads 360" through which the string 352a" extends. Preferably, the knots 394a are located diametrically opposite (or close to that location) the block 392a about the pad 350". From connection block 392b, ends of string 352b" are routed around an upper pin 380b so that the string 352b" extends circumferentially around the compression pad 350". Ends of the string 352b" are formed into knots 392b adjacent to beads 360" through which the string 352b" extends. Preferably, the knots 394b are located diametrically opposite (or close to that location) the block 392b about the pad 350". From connection block 392c, ends of string 352c" are routed around an upper pin 380c so that the string 352c" extends circumferentially around the compression pad 350". Ends of the string 352c" are formed into knots 392c adjacent to beads 360" through which the string 352c" extends. Preferably, the knots 394c are located diametrically opposite (or close to that location) the block 392c about the pad 350".

Also, the connection blocks 392a, 392b, and 392c are respectively connected to wires 356a", 356b", and 356c", which are also operably connected to gearbox 312". The blocks 392a, 392b, and 392c are operably moved up and down in the module 354" by movement of the cables 356a", 356b", and 356c", which is caused by operation of the gearbox 312". The blocks 392a, 392b, and 392c are operably moved by the cables 356a", 356b", and 356c" and gearbox 312" to move the respective strings 352a", 352b", and 352c" relative to the pad 350 to cause compression of the breast 306, as described in greater detail below.

Each string 352a", 352b", and 352c" passes from the compression pad 350" through the sides of the module 354" and extends to their respective pins 380a, 380b, and 380c, and each respective string is routed upward from each respective pin to their respective blocks 392a, 392b, and 392c. The pins 380a, 380b, and 380c are located within module 354" so that the strings 352a", 352b", and 352c" are turned through respective angles $\Theta_a$, $\Theta_b$, and $\Theta_c$ so that the strings 352a", 352b", and 352c" are routed upwardly to the respective blocks 392a, 392b, and 392c. Thus, the pins 380a, 380b, and 380c can provide mechanical advantage for the gearbox 312" to pull the strings 352a", 352b", and 352c" so that when the strings are pulled, the tension in the strings will cause compression of the breast 306 to be radially directed substantially all the way around the breast 306. In one embodiment, the angles $\Theta_a$, $\Theta_b$, and $\Theta_c$ may be in a range of 100° and 160°.

There have been described and illustrated herein several embodiments of a breast milk expression system and apparatus. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other suitable materials may be used as well. In addition, while particular types of driving units have been disclosed, it will be understood that other arrangements of driving units can be used, such as, by way of example, and not by way of limitation, a motorized worm drive, and an electro-magnetic solenoid. Further, while particular embodiments using two or three strings for applying compression have been shown, it will be appreciated that four or more strings may also be utilized. The number or strings may be related to cup size. Also, while a system having two expression apparatuses is preferred, it will be recognized that a single expression apparatus system may also be used. Moreover, while particular configurations have been disclosed in reference to the straps used to position the expression apparatuses, it will be appreciated that other configurations could be used as well. It will therefore be appreciated by those skilled in the art that yet other modifications could be made to the provided invention without deviating from its spirit and scope as claimed.

What is claimed is:

1. A breast milk expression apparatus comprising:
    at least one compression pad disposable about a breast of a user and configured for radial displacement relative to the breast, the at least one compression pad having a concave inner surface configured to engage an outer surface of the breast and a tapered outer surface disposed opposite the concave inner surface;

a plurality of cables that extend circumferentially about the tapered outer surface of the at least one compression pad at different positions relative to the torso of the user and that are displaceable relative to the tapered outer surface of the at least one compression pad; and a unit operably coupled to the plurality of cables and configured to apply a compression-expansion cycle to the plurality of cables, wherein the compression-expansion cycle includes compression operations that pull on the plurality of cables to sequentially apply tension to the plurality of cables without removal of tension from the plurality of cables and displace the at least one compression pad radially inwardly against the breast to cause compression of the breast, and wherein the compression-expansion cycle further includes expansion operations that remove tension from the plurality of cables to permit expansion of the breast;

wherein the unit includes a plurality of pull members that are connected to corresponding cables of the plurality of cables and configured to move linearly to pull on the cables and sequentially apply tension to the plurality of cables without removal of tension from the plurality of cables during the compression operations of the compression-expansion cycle.

2. The apparatus according to claim 1, wherein the unit is configured to vary at least one of a pressure applied by the at least one compression pad to the breast, a duration of the compression operations, a duration of the expansion operations, and a heating level of the at least one compression pad.

3. The apparatus according to claim 1, further comprising: an outer shell coupled to the at least one compression pad.

4. The apparatus according to claim 3, wherein the outer shell defines a central opening dimensioned to receive a breast pump breastshield therethrough for engagement with the user's breast.

5. The apparatus according to claim 3, further comprising a cover configured to at least partially cover the outer shell, the at least one compression pad, and the unit.

6. The apparatus according to claim 1, further comprising a plurality of beads fixed to the tapered outer surface of the at least one compression pad and through which the plurality of cables extends, the beads being circumferentially spaced from one another around the tapered outer surface of the at least one compression pad, wherein the plurality of cables are configured to slide in the beads.

7. The apparatus according to claim 1, wherein the at least one compression pad is a single compression pad.

8. The apparatus according to claim 1, wherein the plurality of pull members are part of a transmission unit driven by a motor, wherein linear movement of the plurality of pull members is driven by motor.

9. The apparatus according to claim 1, further comprising a cable routing unit configured to route the plurality of cables from the at least one compression pad to the unit.

10. The apparatus according to claim 1, wherein the at least one compression pad is configured to connect to a bra that is configured to support the at least one compression pad in engagement with the breast of the user.

11. The apparatus according to claim 1, further comprising a power supply configured to supply power to the unit.

12. The apparatus according to claim 1, wherein the tapered outer surface of the at least one compression pad defines a plurality of circumferential channels corresponding to the plurality of cables, wherein the plurality of circumferential channels receive the plurality of cables to permit the plurality of cables to extend through the plurality of circumferential channels and move relative to the tapered outer surface of the at least one compression pad.

13. The apparatus according to claim 1, wherein the at least one compression pad defines a central opening dimensioned to receive a breast pump breastshield therethrough for engagement with the user's breast.

14. The apparatus according to claim 1, wherein:
the plurality of cables comprise an inner cable and an outer cable, the inner cable being closest to the torso of the user, and the outer cable being furthest from the torso of the user; and
the unit is configured such that, during the compression operations, the plurality of pull members pull on the corresponding cables to sequentially apply tension to the plurality of cables from the inner cable to the outer cable without removal of tension from the plurality of cables.

15. The apparatus according to claim 1, wherein:
the plurality of cables comprise an inner cable and an outer cable, the inner cable being closest to the torso of the user, and the outer cable being furthest from the torso of the user; and
the unit is configured such that, during the compression operations, the plurality of pull members pull on the corresponding cables to sequentially apply tension to the plurality of cables from the inner cable to the outer cable without removal of tension from the plurality of cables such that the inner cable is under tension longer than the outer cable.

16. The apparatus according to claim 1, wherein:
the tapered outer surface extends longitudinally from a larger diameter first end to a smaller diameter second end; and
the plurality of cables comprises first, second and third cables that extend circumferentially about the tapered outer surface of the at least one compression pad at corresponding first, second and third longitudinal positions, respectively, wherein the first longitudinal position of the first cable is disposed closer to the first end of the tapered outer surface than the second and third longitudinal positions of the second and third cables, and the second longitudinal position of the second cable is disposed closer to the first end of the tapered outer surface than the third longitudinal position of the third cable.

17. The apparatus according to claim 16, wherein, during the compression operations, the first cable applies compression to the breast first followed by compression applied by the second cable and further followed by compression applied by the third cable such that the breast is compressed progressively in an outward direction toward the nipple area of the breast.

18. The apparatus according to claim 16, wherein, during the compression operations, the first, second and third cables are in tension for corresponding first, second and third time periods, respectively, wherein the first time period is longer than the second and third time periods, and wherein the second time period is longer than the third time period.

19. The apparatus according to claim 1, wherein:
the plurality of cables comprise an inner cable and an outer cable, the inner cable being closest to the torso of the user, and the outer cable being furthest from the torso;
the plurality of pull members comprise an inner pull member and an outer pull member, the inner pull member being connected to the inner cable, and the outer pull member being connected to the outer cable; and the unit is configured to delay linear movement of the outer pull member while the inner pull member moves linearly during a first part of the compression operations, and the unit is further configured to drive linear movement of both the inner pull member and the outer pull member during a second part of the compression operations subsequent to the first part.

20. A breastmilk expression system comprising:

at least one breast milk expression apparatus according to claim 1;

at least one strap coupled to the at least one breast milk expression apparatus and configured to position the at least one breast milk expression apparatus on respective user's breasts; and a controller configured to control the operation of the at least one breast milk expression apparatus.

21. The system of claim 20, wherein the at least one strap comprises a bra, wherein the bra has an inner layer and an outer layer and at least a portion of the at least one breast milk expression apparatus is configured to be connected to the bra between the inner and outer layer.

22. The system of claim 21, wherein a portion of the inner layer is formed as an inner bra cup and a portion of the outer layer is formed as an outer bra cup configured to align with and fold over the inner bra cup in a first configuration and to move out of alignment with the inner bra cup in a second configuration, wherein outer bra cup is in the second configuration when the at least one breast milk expression apparatus is connected to the bra.

23. The system of claim 22, wherein the inner bra cup defines a hole that is configured to align with a hole in the breast milk expression apparatus when the breast milk expression apparatus is connected to the bra, wherein the hole in the inner bra cup and the hole in the breast milk expression apparatus are configured to receive a tubular portion of a breastshield.

24. The system according to claim 21, wherein the at least one compression pad of the breast milk expression apparatus is configured to connect to the inner layer of the bra.

25. The system according to claim 24, wherein the at least one compression pad includes a first connector configured to removably connect to a second connector secured to an inner layer of the bra located about a base of a cup of the bra.

26. The system according to claim 25, wherein the first and second connectors are slide connectors or zipper connectors.

27. The system according to claim 25, wherein a portion of the inner layer is formed as an inner bra cup and the second connector secured to the inner layer of the bra extends about at least portion of a lower half of the base of the inner bra cup.

28. The system according to claim 20, further comprising at least one of a heating pad, a cooling pad, and a medicated pad configured to couple to the at least one strap, wherein the heating pad, cooling pad, medicated pad, and breast milk expression apparatus are configured to interchangeably couple to the at least one strap.

* * * * *